(12) United States Patent
Wang

(10) Patent No.: US 9,550,989 B2
(45) Date of Patent: Jan. 24, 2017

(54) RATIONAL DESIGN OF MICRORNA-SIRNA CHIMERAS FOR MULTI-FUNCTIONAL TARGET SUPPRESSION

(71) Applicant: Washington University, St. Louis, MO (US)

(72) Inventor: Xiaowei Wang, St. Louis, MO (US)

(73) Assignee: WASHINGTON UNIVERSITY, St. Louis, MO (US)

(*) Notice: Subject to any disclaimer, the term of this patent is extended or adjusted under 35 U.S.C. 154(b) by 0 days.

(21) Appl. No.: 14/506,131

(22) Filed: Oct. 3, 2014

(65) Prior Publication Data
US 2015/0099793 A1  Apr. 9, 2015

Related U.S. Application Data

(60) Provisional application No. 61/886,429, filed on Oct. 3, 2013.

(51) Int. Cl.
| C07H 21/02 | (2006.01) |
| C07H 21/04 | (2006.01) |
| C12N 15/11 | (2006.01) |
| C12N 15/113 | (2010.01) |

(52) U.S. Cl.
CPC ......... *C12N 15/111* (2013.01); *C12N 15/1135* (2013.01); *C12N 15/1137* (2013.01); *C12N 2310/14* (2013.01); *C12N 2310/141* (2013.01); *C12N 2310/3519* (2013.01); *C12N 2320/11* (2013.01); *C12Y 207/11001* (2013.01)

(58) Field of Classification Search
CPC .......................... C12N 15/113; C12N 2310/11
See application file for complete search history.

(56) References Cited

U.S. PATENT DOCUMENTS

| 7,888,035 B2 * | 2/2011 | Klass ................ | C12Q 1/6809 435/6.14 |
| 2001/0053519 A1 | 12/2001 | Fodor et al. | |
| 2012/0021983 A1 * | 1/2012 | Tsichlis ............. | C12Q 1/6886 514/8.5 |
| 2012/0283319 A1 * | 11/2012 | Esau .................. | C12N 15/111 514/44 R |

OTHER PUBLICATIONS

Yamanaka et al. (BJU International, 2006, 97, 1300-1308).*
Doench et al. (Genes & Development, 17, 438-442, 2003).*
Ambros, "The functions of animal microRNAs", Nature, 2004, pp. 350-355, vol. 431.
Anderson et al., "Experimental validation of the importance of seed complement frequency to siRNA specificity", RNA, 2008, pp. 853-861, vol. 14, No. 5.
Bellacosa et al., "Activation of AKT Kinases in Cancer: Implications for Therapeutic Targeting", Advances in Cancer Research, 2005, pp. 29-86, vol. 94.

Birmingham et al., "3' UTR seed matches, but not overall identity, are associated with RNAi off-targets", Nature Methods, 2006, pp. 199-204, vol. 3, No. 3.
Calin et al., "MicroRNA signatures in human cancers", Nature Reviews/Cancer, 2006, pp. 857-866, vol. 6.
Croce, "Causes and consequences of microRNA dysregulation in cancer", Nature Reviews/Genetics, 2009, pp. 704-714, vol. 10.
De Guire et al., "Designing small multiple-target artificial RNAs", Nucleic Acids Research, 2010, e140, 8 pgs., vol. 38, No. 13.
Denli et al., "RNAi: an ever-growing puzzle", Trends in Biochemical Sciences, 2003, pp. 196-201, vol. 28, No. 4.
Gregory et al., "The miR-200 family and miR-205 regulate epithelial to mesenchymal transition by targeting ZEB1 and SIP1", Nature Cell Biology, 2008, pp. 593-601, and Supplementary Information pp. 1-7, vol. 10, No. 5.
Grimm et al., "Fatality in mice due to oversaturation of cellular microRNA/short hairpin RNA pathways", Nature, 2006, pp. 537-541, vol. 441.
Hannon, "RNA interference", Nature, 2002, pp. 244-251, vol. 418.
Jackson et al., "Expression profiling reveals off-target gene regulation by RNAi", Nature Biotechnology, 2003, pp. 635-637, vol. 21, No. 6.
Jackson et al., "Position-specific chemical modification of siRNAs reduces "off-target" transcript silencing", RNA, 2006, pp. 1197-1205, vol. 12, No. 7.
Jackson et al., "Recognizing and avoiding siRNA off-target effects for target identification and therapeutic application", Nature Reviews/Drug Discovery, 2010, pp. 57-67, vol. 9.
Johnson et al., "The let-7 MicroRNA Represses Cell Proliferation Pathways in Human Cells", Cancer Research, 2007, pp. 7713-7722, vol. 67, No. 16.
Kent et al., "A small piece in the cancer puzzle: microRNAs as tumor suppressors and oncogenes", Oncogene, 2006, pp. 6188-6196, vol. 25.
Kota et al., "Therapeutic delivery of miR-26a inhibits cancer cell proliferation and induces tumor-specific apoptosis", Cell, 2009, pp. 1005-1017, vol. 137, No. 6.
Kozomara et al., "miRBase: integrating microRNA annotation and deep-sequencing data", Nucleic Acids Research, 2011, pp. D152-D157, vol. 39.
Langmead et al., "Ultrafast and memory-efficient alignment of short DNA sequences to the human genome", Genome Biology, 2009, pp. R25.1-R25.10, vol. 10, No. 3.
Lewis et al., "Conserved Seed Pairing, Often Flanked by Adenosines, Indicates that Thousands of Human Genes are MicroRNA Targets", Cell, 2005, pp. 15-20, vol. 120.
Lim et al., "Microarray analysis shows that some microRNAs downregulate large Numbers of target mRNAs", Nature, 2005, pp. 769-773, vol. 433.
Ma et al., "miR-9, a MYC/MYCN-activiated microRNA, regulates E-cadherin and cancer metastasis", Nature Cell Biology, 2010, pp. 247-256, and Supplementary Information, vol. 12, No. 3.

(Continued)

*Primary Examiner* — Amy Bowman
(74) *Attorney, Agent, or Firm* — Polsinelli PC

(57) ABSTRACT

The present disclosure encompasses methods for rational design of microRNA and small interfering RNA chimeras and compositions and methods of use thereof.

7 Claims, 8 Drawing Sheets
(8 of 8 Drawing Sheet(s) Filed in Color)

(56) References Cited

OTHER PUBLICATIONS

Mestdagh et al., "The microRNA body map: dissecting microRNA function through integrative genomics", Nucleic Acids Research, 2011, e136, 8 pgs, vol. 39, No. 20.
Miranda et al., "A Pattern-Based Method for the Identification of MicroRNA Binding Sites and Their Corresponding Heteroduplexes", Cell, 2006, pp. 1203-1217, vol. 126.
Miska, "How microRNAs control cell division, differentiation and death", Current Opinion in Genetics & Development, 2005, pp. 563-568, vol. 15.
Nielsen et al., "Determinants of targeting by endogenous and exogenous microRNAs and siRNAs", RNA, 2007, pp. 1894-1910, vol. 13.
Nishimura et al., "Therapeutic Synergy between microRNA and siRNA in Ovarian Cancer Treatment", Cancer Discovery, 2013, pp. 1302-1315, vol. 3.
Park et al., "The miR-200 family determines the epithelial phenotype of cancer cells by targeting the E-cadherin repressors ZEB1 and ZEB2", Genes & Development, 2008, pp. 894-907, vol. 22.
Rossi, "New Hope for a MicroRNA Therapy for Liver Cancer", Cell, 2009, pp. 990-992, vol. 137.
Saetrom, "Designing Dual-Targeting siRNA Duplexes Having Two Active Strands that Combine siRNA and MicroRNA-Like Targeting", Methods in Molecular Biology, 2013, pp. 169-177, vol. 942.
Scheffner et al., "The E6 Oncoprotein Encoded by Human Papillomavirus Types 16 and 18 Promotes the Degradation of p53", Cell, 1990, pp. 1129-1136, vol. 63.
Sontheimer, "Assembly and Function of RNA Silencing Complexes", Nature Reviews/Molecular Cell Biology, 2005, pp. 127-138, vol. 6.
Tiemann et al., "Dual-targeting siRNAs", RNA, 2010, pp. 1275-1284, vol. 16, No. 6.
Tong et al., "Modulation of miRNA activity in human cancer: a new paradigm for cancer gene therapy?", Cancer Gene Therapy, 2008, pp. 341-355, vol. 15.
Valastyan et al., "A Pleiotropically Acting microRNA, miR-31, Inhibits Breast Cancer Metastasis", Cell, 2009, pp. 1032-1046, vol. 137, No. 6.
Wang et al., "A PCR primer bank for quantitative gene expression analysis", Nucleic Acids Research, 2003, e154, 8 pgs., vol. 31, No. 24.
Wang et al., "Prediction of both conserved and nonconserved microRNA targets in animals", Bioinformatics, 2008, pp. 325-332, vol. 24, No. 3.
Wang, "miRDB: A microRNA target prediction and functional annotation database with a wiki interface", RNA, 2008, pp. 1012-1017, vol. 14, No. 6.
Wang et al., "Selection of hyperfunctional siRNAs with improved potency and specificity", Nucleic Acids Research, 2009, e152, 9 pgs., vol. 37, No. 22.
Wang et al., "NF-kappaB P50/P65 hetero-dimer mediates differential regulation of CD166/ALCAM expression via interaction with micoRNA-9 after serum deprivation, providing evidence for a novel negative auto-regulatory loop", Nucleic Acids Research, 2011, pp. 6440-6455, vol. 39, No. 15.
Wang et al., "PrimerBank: a PCR primer database for quantitative gene expression analysis, 2012 update", Nucleic Acids Research, 2012, pp. D1144-D1149, vol. 40, Database issue.
Wurdinger et al., "Molecular therapy in the microRNA era", The Pharmacogenomics Journal, 2007, pp. 297-304, vol. 7.
Zhang et al., "Examination of Artificial MiRNA Mimics with Centered-Site Complementarity for Gene Targeting", PLoS One, 2013, e72062, 7 pgs., vol. 8, No. 8.

\* cited by examiner

A

```
miR-200a     UAACACUGUCUGGUAACGAUGU
aiR-200a-1   UAACACUGCCCUACGUGAAUC
aiR-200a-2   UAACACUGUUAAACCUUGCUC
aiR-200a-3   AAACACUGCUCCUCUGUCCCA
```

B

C

D

A

B

A

```
miR-9      UCUUUGGUUAUCUAGCUGUAUGA
aiR-9-1    UCUUUGGUUAGUACGGUGAAG
aiR-9-2    UCUUUGGUUGGGGAGAGGAGC
aiR-9-3    UCUUUGGUCCCAGCUACUCCG
```

B

A

B

Figure 8 aiR-200a-3 shRNA-1

Structure (SEQ ID NO:13):

```
---ccgg         uu           c         ag
      ggacaga   agcagug   uuccc    a
      |||||||   |||||||   |||||
      ccugucu   ucgucac   aaggg    a
guuuua          cc           a         uu
```

Sequence (SEQ ID NO:14):

ccggggacagattagcagtgcttcccagaattgggaa
acactgctcctctgtcccatttttg (63)

aiR-200a-3 shRNA-2

Structure (SEQ ID NO:15):

```
----ccgg        uu           c         ag
      ggacaga   agcagug   uuccu    a
      |||||||   |||||||   |||||
      ccugucu   ucgucac   aagga    g
guuuuaa         cc           a         gu
```

Sequence (SEQ ID NO:16):

ccggggacagattagcagtgcttcctagagtgaggaaa
cactgctcctctgtccaattttg (62)

SEQUENCE LISTING

```
<160> NUMBER OF SEQ ID NOS: 16

<210> SEQ ID NO 1
<211> LENGTH: 22
<212> TYPE: RNA
<213> ORGANISM: Artificial Sequence
<220> FEATURE:
<223> OTHER INFORMATION: SYNTHESIZED

<400> SEQUENCE: 1
uaacacuguc ugguaacgau gu                                              22

<210> SEQ ID NO 2
<211> LENGTH: 22
<212> TYPE: RNA
<213> ORGANISM: Artificial Sequence
<220> FEATURE:
<223> OTHER INFORMATION: SYNTHESIZED

<400> SEQUENCE: 2
uaacacuguc ugguaaagau gg                                              22

<210> SEQ ID NO 3
<211> LENGTH: 22
<212> TYPE: RNA
<213> ORGANISM: Artificial Sequence
<220> FEATURE:
<223> OTHER INFORMATION: SYNTHESIZED
```

<400> SEQUENCE: 3
uaauacugcc ugguaaugau ga                                          22

<210> SEQ ID NO 4
<211> LENGTH: 23
<212> TYPE: RNA
<213> ORGANISM: Artificial Sequence
<220> FEATURE:
<223> OTHER INFORMATION: SYNTHESIZED

<400> SEQUENCE: 4
uaauacugcc ggguaaugau gga                                         23

<210> SEQ ID NO 5
<211> LENGTH: 22
<212> TYPE: RNA
<213> ORGANISM: Artificial Sequence
<220> FEATURE:
<223> OTHER INFORMATION: SYNTHESIZED

<400> SEQUENCE: 5
uaacucuguc ugguaaaacc gu                                          22

<210> SEQ ID NO 6
<211> LENGTH: 21
<212> TYPE: RNA
<213> ORGANISM: Artificial Sequence
<220> FEATURE:
<223> OTHER INFORMATION: SYNTEHSIZED

<400> SEQUENCE: 6
uaacacugcc cuacgugaau c                                           21

<210> SEQ ID NO 7
<211> LENGTH: 21
<212> TYPE: RNA
<213> ORGANISM: Artificial Sequence
<220> FEATURE:
<223> OTHER INFORMATION: SYNTEHSIZED

<400> SEQUENCE: 7
uaacacuguu aaaccuugcu c                                           21

<210> SEQ ID NO 8
<211> LENGTH: 21
<212> TYPE: RNA
<213> ORGANISM: Artificial Sequence
<220> FEATURE:
<223> OTHER INFORMATION: SYNTHESIZED

<400> SEQUENCE: 8
uaacacugcu ccucuguccc a                                           21

<210> SEQ ID NO 9
<211> LENGTH: 23
<212> TYPE: RNA
<213> ORGANISM: Artificial Sequence
<220> FEATURE:
<223> OTHER INFORMATION: SYNTHESIZED

<400> SEQUENCE: 9
ucuuugguua ucuagcugua uga                                         23

<210> SEQ ID NO 10
<211> LENGTH: 21

```
<212> TYPE: RNA
<213> ORGANISM: Artificial Sequence
<220> FEATURE:
<223> OTHER INFORMATION: SYNTHESIZED

<400> SEQUENCE: 10
ucuuugguua guacggugaa g                                           21

<210> SEQ ID NO 11
<211> LENGTH: 21
<212> TYPE: RNA
<213> ORGANISM: Artificial Sequence
<220> FEATURE:
<223> OTHER INFORMATION: SYNTHESIZED

<400> SEQUENCE: 11
ucuuugguug gggagaggag c                                           21

<210> SEQ ID NO 12
<211> LENGTH: 21
<212> TYPE: RNA
<213> ORGANISM: Artificial Sequence
<220> FEATURE:
<223> OTHER INFORMATION: SYNTHESIZED

<400> SEQUENCE: 12
ucuuuggucc cagcuacucc g                                           21

<210> SEQ ID NO 13
<211> LENGTH: 63
<212> TYPE: RNA
<213> ORGANISM: Artificial Sequence
<220> FEATURE:
<223> OTHER INFORMATION: SYNTHESIZED

<400> SEQUENCE: 13
ccgggggaca gauuagcagu gcuucccaga auugggaaac acugcuccuc ugucccauuu  60
uug                                                               63

<210> SEQ ID NO 14
<211> LENGTH: 63
<212> TYPE: DNA
<213> ORGANISM: Artificial Sequence
<220> FEATURE:
<223> OTHER INFORMATION: SYNTHESIZED

<400> SEQUENCE: 14
ccgggggaca gattagcagt gcttcccaga attgggaaac actgctcctc tgtcccattt  60
ttg                                                               63

<210> SEQ ID NO 15
<211> LENGTH: 62
<212> TYPE: RNA
<213> ORGANISM: Artificial Sequence
<220> FEATURE:
<223> OTHER INFORMATION: SYNTHESIZED

<400> SEQUENCE: 15
ccggggacag auuagcagug cuuccuagag ugaggaaaca cugcuccucu guccaauuuu  60
ug                                                                62

<210> SEQ ID NO 16
<211> LENGTH: 62
<212> TYPE: DNA
```

```
<213> ORGANISM: Artificial Sequence
<220> FEATURE:
<223> OTHER INFORMATION: SYNTHESIZED

<400> SEQUENCE: 16
ccggggacag attagcagtg cttcctagag tgaggaaaca ctgctcctct gtccaatttt    60
tg                                                                   62
```

RATIONAL DESIGN OF MICRORNA-SIRNA CHIMERAS FOR MULTI-FUNCTIONAL TARGET SUPPRESSION

CROSS REFERENCE TO RELATED APPLICATIONS

This application claims the priority of U.S. provisional application No. 61/886,429, filed Oct. 3, 2013, which is hereby incorporated by reference in its entirety.

GOVERNMENTAL RIGHTS

This invention was made with government support under R01GM089784 awarded by the NIH. The government has certain rights in the invention.

FIELD OF THE INVENTION

The present disclosure relates to methods for rational design of microRNA and small interfering RNA chimeras and compositions and methods of use thereof. The present disclosure results in improved RNAi-based therapeutics.

BACKGROUND OF THE INVENTION

RNA interference (RNAi) is an RNA-guided gene silencing process within living cells that controls the expression of the targeted genes (Hannon 2002; Denli and Hannon 2003; Sontheimer 2005). There are two major types of small RNA molecules that are central to RNA interference, microRNAs (miRNAs) and small interfering RNAs (siRNAs).

MicroRNAs (miRNAs) are involved in a variety of human diseases by simultaneously suppressing many gene targets. Thus, the therapeutic value of miRNAs has been intensely studied. However, there are potential limitations with miRNA-based therapeutics such as relatively moderate impact on gene target regulation and cellular phenotypic control. Further, there are only a limited number of natural miRNAs to be used in RNAi. In contrast, siRNAs may result in efficient knockdown of a target gene, but may only target one gene at a time. Thus, there is a need in the art for miRNA-based therapeutics that are rationally designed to improve the efficiency of knockdown and are multi-functional to simultaneously target multiple genes.

SUMMARY OF THE INVENTION

In an aspect, the disclosure encompasses a method for disrupting expression of at least two target nucleic acids simultaneously. The method comprises selecting at least two target nucleic acids; contacting the at least two target nucleic acids with a nucleic acid construct comprising a nucleotide sequence of about 19 to about 25 nucleotides in which nucleotides 2 through 8 are identical to nucleotides 2 through 8 of an miRNA that targets at least one of the at least two target nucleic acids and the rest of the nucleotides are identical to those of a siRNA that targets one of the at least two target nucleic acids, and wherein the nucleotide sequence is capable of specifically hybridizing to the at least two target nucleic acids; and measuring expression of the at least two target nucleic acids, wherein a disruption in expression indicates hybridization of the nucleotide sequence to the at least two target nucleic acids.

In another aspect, the disclosure encompasses a composition comprising a nucleic acid construct comprising a nucleotide sequence of about 19 to about 25 nucleotides in which nucleotides 2 through 8 are identical to nucleotides 2 through 8 of an miRNA that targets at least one of at least two target nucleic acids and the rest of the nucleotides are identical to those of a siRNA that targets one of the at least two target nucleic acids, wherein the nucleotide sequence is capable of specifically hybridizing to the at least two target nucleic acids.

BRIEF DESCRIPTION OF THE FIGURES

The application file contains at least one drawing executed in color. Copies of this patent application publication with color drawing(s) will be provided by the Office upon request and payment of the necessary fee.

FIG. 8 depicts hairpin shRNAs of aiR-200a-3 to stably express the aiRNA using a lentiviral delivery system. The aiR-200a-3 sequences are highlighted in red. aiR-200a-3 shRNA-1 (Structure—SEQ ID NO:13—CCGGGGGACA-GAUUAGCAGUGCUUCCCAGAAUUGGGAAACA-CUGCUCCUCUGUCCCAUUUUUG; Sequence—SEQ ID NO:14—CCGGGGGACAGATTAGCAGTGCTTCCCA-GAATTGGGAAACACTGCTCCTCTGTCCCATTTTTG) and aiR-200a-3 shRNA-2 (Structure—SEQ ID NO:15—CCGGGGACAGAUUAGCAGUGCUUCCUA-GAGUGAGGAAACACUGCUCCUCUGUC-CAAUUUUUG; Sequence—SEQ ID NO:16—CCGGGGACAGATTAGCAGTGCTTCCTAGAGTGAGG AAACACTGCTCCTCTGTCCAATTTTTG)

DETAILED DESCRIPTION OF THE INVENTION

Figure 1:
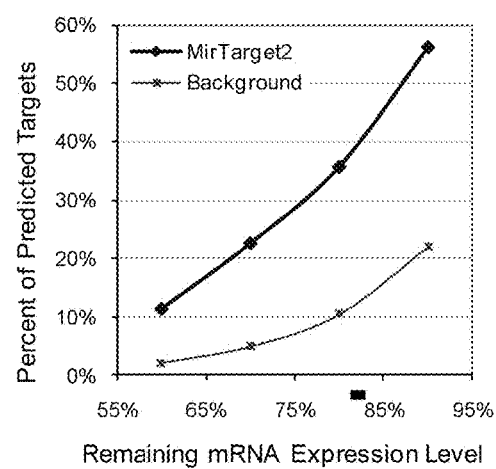
FIG. 1 depicts a graph showing microarrays to validate predicted siRNA off-targets. An siRNA targeting GAPDH was transfected in HeLa cells, and the transcripts downregulated by the siRNA were globally identified with microarrays 24 hours post transfection. The graph shows the fraction of downregulated off-targets among all off-targets predicted by MirTarget2 at various gene knockdown levels (represented by remaining RNA expression level). Gene downregulation was determined by referencing to the negative control transfections.

To improve upon RNAi-based therapeutics, the inventors have developed chimeric small RNAs (aiRNAs) by incorporating sequences from both miRNAs and siRNAs. These aiRNAs not only inherit functions from natural miRNAs, but also gain new functions of gene knockdown in an siRNA-like fashion resulting in improved efficacy of multifunctional aiRNAs. Specifically, an aiRNA that inherits the functions of both miR-200a and AKT1-targeting siRNA for simultaneous suppression of cancer cell motility and proliferation has been developed. These general principles of aiRNA design may be used to engineer new aiRNAs mimicking other miRNAs and siRNAs. By regulating multiple cellular functions, aiRNAs result in an improved tool over miRNAs to target disease-related genes, thus alleviating dependency on a limited number of miRNAs for the development of RNAi-based therapeutics.

I. Methods

The present disclosure encompasses a method for disrupting expression of at least two target nucleic acids simultaneously. The method comprises selecting at least two target nucleic acids; contacting the at least two target nucleic acids with a nucleic acid construct comprising a nucleotide sequence of about 19 to about 25 nucleotides in which nucleotides 2 through 8 are identical to nucleotides 2 through 8 of an miRNA that targets at least one of the at least two target nucleic acids and the rest of the nucleotides are identical to those of a siRNA that targets one of the at least two target nucleic acids and wherein the nucleotide sequence is capable of specifically hybridizing to the at least two target nucleic acids; and measuring expression of the at least two target nucleic acids, wherein a disruption in expression indicates hybridization of the nucleotide sequence to the at least two target nucleic acids.

(a) Selecting at Least Two Target Nucleic Acids

A method of the invention begins with the selection of at least two target nucleic acids whose function is to be modulated. This may be, for example, a cellular nucleic acid (or mRNA transcribed from the nucleic acid) whose expression is associated with a particular disorder or disease state, or a nucleic acid from an infectious agent. Simultaneously targeting nucleic acids from multiple functional categories that are related to the same disease may enhance the therapeutic efficacy of RNA interference. For example, selecting a target nucleic acid that is known to be overexpressed in cancer, an oncogene in cancer, and/or involved in cancer pathogenesis, metastasis, or aggressiveness. In an embodiment, the target nucleic acids may be selected from a group consisting nucleic acids involved in proliferation, nucleic acids involved in cell motility, and nucleic acids involved in cell migration. In the present invention, the at least two target nucleic acids is a nucleic acid molecule encoding AKT1 and nucleic acid molecules regulated by miR-200a. The selecting process also includes determination of a site or sites within this nucleic acid for the interaction with a nucleotide sequence of the invention to occur such that the desired effect, e.g., detection, modulation, or disruption of expression of the target nucleic acid, or protein thereof, will result. This is described in further detail below.

(b) Contacting at Least Two Target Nucleic Acids with a Nucleic Acid Construct

A method of the invention comprises contacting at least two target nucleic acids with a nucleic acid construct. The contact may occur in vitro or in vivo. Any suitable method known in the art of contacting a nucleic acid construct and target nucleic acids may be used. The contact may occur using transfection. For example, a cell comprising target nucleic acids may be transfected with a nucleic acid construct of the invention. Methods of transfecting a cell are known in the art. Alternatively, the contact may occur by stably expressing a nucleotide sequence of the invention in a cell comprising target nucleic acids. For example, an expression vector comprising a nucleotide sequence of the invention may be used to express the nucleotide sequence in a cell. This is described in further detail below.

A nucleic acid construct of the invention comprises a nucleotide sequence of about 19 to about 25 nucleotides in which nucleotides 2 through 8 are identical to nucleotides 2 through 8 of an miRNA that targets at least one of the at least two target genes and the rest of the nucleotides are identical to those of a siRNA that targets one of the at least two target genes.

A nucleic acid construct of the invention comprises a nucleotide sequence. The nucleotide sequence may be about 15 to about 30 nucleotides. For example, the nucleotide sequence may be about 15 to about 19 nucleotides, about 19 to about 23 nucleotides, about 23 to about 27 nucleotides, or about 27 to about 30 nucleotides. In a specific embodiment, the nucleotide sequence may be about 19 to about 25 nucleotides. For example, the nucleotide sequence may be 15, 16, 17, 18, 19, 20, 21, 22, 23, 24, 25, 26, 27, 28, 29 or 30 nucleotides. In a specific embodiment, the nucleotide sequence may be 21 nucleotides. In another specific embodiment, the nucleotide sequence may be 22 nucleotides.

A nucleotide sequence comprises nucleotides from an miRNA and nucleotides from a siRNA. Such a miRNA-siRNA chimera may be referred to as an artificial interference RNA (aiRNA). As used herein, the term "aiRNA" refers to a non-natural RNA molecule that has a similar sequence length to naturally processed mature miRNAs and comprises both miRNA and siRNA sequences. The aiRNA molecules are designed based on natural miRNA as well as siRNA sequences. The aiRNAs of the invention function as natural miRNAs and also function in gene knockdown via an siRNA-like mechanism.

As used herein, the term "miRNA" refers to a small (e.g. generally less than 30 nucleotides) non-coding RNA molecule which functions in transcriptional and post-transcriptional regulation of gene expression. A miRNA functions via base-pairing with complementary sequences within mRNA molecules, usually resulting in gene silencing via translational repression or target degradation. A mature miRNA is processed through a series of steps from a larger primary RNA transcript (pri-miRNA), or from an intron comprising a miRNA (mirtron), to generate a stem loop pre-miRNA structure comprising the miRNA sequence. A pre-miRNA is then cleaved to generate the mature miRNA. A miRNA may be a pri-miRNA, a pre-miRNA, or a mature miRNA. A miRNA may also be a mirtron miRNA. In non-limiting examples, the miRNA is a mature miRNA.

Over two thousand human miRNAs have been identified. Any suitable miRNA may be used in the invention. Suitable miRNAs to be used in the invention may be found via databases such as miRBase described in Kozomara et al., *Nucleic Acids Res* 2011; 39:D152-7, which is hereby incorporated by reference in its entirety. In an embodiment, a miRNA is a miR-200 family miRNA including, but not limited to, miR-200a, miR-141, miR-200b, miR-200c, and miR-429. miR-200a may comprise SEQ ID NO:1. In an embodiment, miR-141 comprises SEQ ID NO:2, miR-200b comprises SEQ ID NO:3, miR-200c comprises SEQ ID NO:4, and miR-429 comprises SEQ ID NO:5. In another embodiment, miR-141 consists of SEQ ID NO:2, miR-200b consists of SEQ ID NO:3, miR-200c consists of SEQ ID NO:4, and miR-429 consists of SEQ ID NO:5. In a specific embodiment, a miRNA is miR-200a. In another specific embodiment, a miRNA is miR-141. In another embodiment, a miRNA is miR-9 (SEQ ID NO:9).

An miRNA may be chosen based on the nucleic acids it regulates. An miRNA generally regulates more than one nucleic acid. For example, an miRNA may regulate 1, 2, 3, 4, 5, 6, 7, 8, 9, 10 or more nucleic acids. Accordingly, an miRNA may regulate 10, 15, 20, 25, 30, 35, 40, 45, 50, 55, 60, 65, 70, 75, 80, 85, 90, 95, 100 or more nucleic acids. One of skill in the art will be able to determine the nucleic acids regulated by an miRNA. Numerous databases exist to determine nucleic acids regulated by an miRNA. For example, MirTarget2 may be used for miRNA target prediction. For more details, please see Wang, *RNA* 2009; 14:1012-1017, which is hereby incorporated by reference in its entirety. Alternatively, the microRNA body map may be used to determine miRNA function as described in Mestdagh et al, *Nucleic Acids Res* 2011; 39(20):e136, which is hereby incorporated by reference in its entirety. By way of non-limiting example, if suppression of motility of cancer cells is the desired function, the miR-200 family may be chosen. Alternatively, if promotion of motility of cancer cells is the desired function, miR-9 may be chosen. One of skill in the art, would be able to choose the miRNA based on the desired function to be altered using the databases described herein, as well as others available in the art. In an embodiment, a miRNA of the invention may targets nucleic acids involved in proliferation, nucleic acids involved in cell motility and/or nucleic acids involved in cell migration.

An aiRNA nucleotide sequence of the invention comprises a seed region of an miRNA. The seed region is a 7-8 nucleotide motif in the miRNA that determines specificity of binding of an miRNA to a target mRNA regulated by the miRNA. The seed region, also referred to as the seed sequence, is the most critical determinant for miRNA target specificity. In most miRNAs, the seed region is within nucleotides 1 through 9 of the mature miRNA sequence. In a specific embodiment, the seed region is within nucleotides 2 through 8 of the mature miRNA sequence.

In an embodiment, nucleotides 2 through 8 of the aiRNA nucleotide sequence are identical to nucleotides 2 through 8 of an miRNA. In another embodiment, nucleotides 1 through 9 of the aiRNA nucleotide sequence are identical to nucleotides 1 through 9 of an miRNA. In still another embodiment, nucleotides 1 through 8 of the aiRNA nucleotide sequence are identical to nucleotides 1 through 8 of an miRNA. In yet still another embodiment, nucleotides 2 through 9 of the aiRNA nucleotide sequence are identical to nucleotides 2 through 9 of an miRNA. A person skilled in the art may be able to determine the sequence of a seed region of an miRNA. In an embodiment, nucleotides 2 through 8 of the aiRNA nucleotide sequence consists of nucleotides 2 through 8 of a miR-200 family miRNA. For example, nucleotides 2 through 8 of the aiRNA nucleotide sequence consists of nucleotides 2 through 8 of SEQ ID NO:1 (miR-200a), SEQ ID NO:2 (miR-141), SEQ ID NO:3 (miR-200b), SEQ ID NO:4 (miR-200c), or SEQ ID NO:5 (miR-429). In a specific embodiment, nucleotides 2 through 8 of the aiRNA nucleotide sequence consists of nucleotides 2 through 8 of SEQ ID NO:1 (miR-200a). In another embodiment, nucleotides 2 through 8 of the aiRNA nucleotide sequence consists of nucleotides 2 through 8 of miR-9 (SEQ ID NO:9).

An aiRNA nucleotide sequence of the invention comprises an miRNA seed sequence and a siRNA sequence. As used herein, the term "siRNA" refers to a small (e.g. generally less than 30 nucleotides) non-coding RNA molecule which functions in transcriptional and post-transcriptional regulation of gene expression. Generally, a siRNA specifically targets 1 nucleic acid. In general, a siRNA comprises a double-stranded RNA molecule that ranges from about 15 to about 29 nucleotides in length. In some embodiments, the siRNA may be 16, 17, 18, 19, 20, 21, 22, 23, 24, 25, 26, 27, 28 or 29 nucleotides in length. In other embodiments, the siRNA may be about 16 to about 18, about 17 to about 19, about 21 to about 23, about 24 to about 27, or about 27 to about 29 nucleotides in length. In a specific embodiment, the siRNA may be about 21 nucleotides in length. In another specific embodiment, the siRNA may be about 22 nucleotides in length. A siRNA may optionally further comprise one or two single-stranded overhangs, e.g., a 5' overhang on one or both ends, a 3' overhang on one or both ends, or a combination thereof. The siRNA may be formed from two RNA molecules that hybridize together or, alternatively, may be generated from a short hairpin RNA (shRNA) (see below). In some embodiments, the two strands of the siRNA may be completely complementary, such that no mismatches or bulges exist in the duplex formed between the two sequences. In other embodiments, the two strands of the siRNA may be substantially complementary, such that one or more mismatches and/or bulges may exist in the duplex formed between the two sequences. In certain embodiments, one or both of the 5' ends of the siRNA may have a phosphate group, while in other embodiments one or both of the 5' ends lack a phosphate group. In other embodiments, one or both of the 3' ends of the siRNA may have a hydroxyl group, while in other embodiments one or both of the 5' ends lack a hydroxyl group.

Any suitable siRNA may be used in the invention. Typically, siRNAs are targeted to exonic sequences of the target nucleic acid. One strand of the siRNA, which is referred to as the "antisense strand" or "guide strand," includes a portion that hybridizes with a target nucleic acid. A target nucleic acid refers to a nucleic acid sequence expressed by a cell for which it is desired expression be disrupted. In the context of a therapeutic composition of the invention, disrupting expression of a target nucleic acid may produce a beneficial effect. Those of skill in the art are familiar with programs, algorithms, and/or commercial services that design siRNAs for target genes. For example, the Rosetta siRNA Design Algorithm (Rosetta Inpharmatics, North Seattle, Wash.), MISSION® siRNA (Sigma-Aldrich, St. Louis, Mo.) and siGENOME siRNA (Thermo Scientific) may be used. In an exemplary example, suitable siRNAs to be used in the invention may be designed using bioinformatics tools such as siOligo described in Wang et al., *Nucleic Acids Res* 2009; 37:e152, which is hereby incorporated by reference in its entirety. Using siOligo, siRNAs are ranked based on their predicted knockdown efficiency. Accordingly, a suitable siRNA may be identified. In certain embodiments, an identified siRNA may have one or more mismatched base pairs with respect to its target nucleic acid, and remains capable of hybridizing to its target sequence. For instance, an identified siRNA may have 1, 2, 3, 4, 5, 6, 7, 8, 9, 10 or more mismatched base pairs with respect to its target nucleic acid, and remains capable of hybridizing to its target sequence. In other embodiments, an identified siRNA is complementary to its target nucleic acid. In preferred embodiments, an identified siRNA is about 70, 75, 80, 85, 90, 95%, or about 100% complementary to its target nucleic acid.

An siRNA may be selected based on the nucleic acid or nucleic acids it regulates. A target nucleic acid refers to a nucleic acid sequence expressed by a cell for which it is desired expression be disrupted. One of skill in the art will be able to determine the nucleic acid or nucleic acids regulated by an siRNA. In a preferred embodiment, the siRNA may be specifically designed to target a desired nucleic acid. By way of non-limiting example, if suppression of cancer cell proliferation is the desired function, the AKT1 nucleic acid may be chosen. One of skill in the art, would be able to choose the siRNA based on the desired function to be altered using the databases described herein, as well as others available in the art. In an embodiment, a siRNA of the invention may targets nucleic acids involved in proliferation. In an specific embodiment, a siRNA is an AKT1 siRNA. In another specific embodiment, a siRNA is a TP53 siRNA.

An aiRNA nucleotide sequence of the invention is designed to comprise a seed sequence of an miRNA and a siRNA sequence. In an embodiment, the antisense strand of the identified siRNA comprises the identical seed sequence as the chosen miRNA seed sequence and the rest of the identified siRNA may be completely complementary with a region of the target nucleic acid, i.e., it hybridizes to the target nucleic acid without a single mismatch or bulge over a target region between about 15 and about 29 nucleotides in length, preferably at least 16 nucleotides in length, and more preferably about 18-22 nucleotides in length. In another embodiment, the antisense strand of the identified siRNA comprises the identical seed sequence as the chosen miRNA seed sequence and the rest of the identified siRNA may not be completely complementary with a region of the target nucleic acid, i.e., it hybridizes to the target nucleic acid with one or more mismatches or bulges over a target region between about 15 and about 29 nucleotides in length, preferably at least 16 nucleotides in length, and more preferably about 18-22 nucleotides in length. In another embodiment, the antisense strand of the identified siRNA may not comprise the identical seed sequence of the chosen miRNA. In such an embodiment, the aiRNA may be designed by introducing a few mismatched bases into the identified siRNA such that the seed sequence of the miRNA is unchanged. Stated another way, a few mismatched bases may be introduced into the identified siRNA such that the aiRNA comprises the seed sequence of the chosen miRNA at nucleotides 1 through 9, or preferably at nucleotides 2 through 8, and the rest of the identified siRNA. Accordingly, the antisense strand may be substantially complementary to the target nucleic acid, i.e., one or more mismatches and/or bulges may exist in the duplex formed by the antisense strand and the target nucleic acid. The one or more mismatches may be only within the seed region or may be within the seed region and outside the seed region provided the resulting aiRNA remains capable of hybridizing to its target sequence. In an embodiment, nucleotides 1 through 9, or preferably nucleotides 2 through 8, of the identified siRNA sequence have 0, 1, 2, 3, or 4 mismatches relative to the nucleotides 1 through 9, or preferably nucleotides 2 through 8, of the aiRNA nucleotide sequence of the invention. Stated another way, an aiRNA nucleotide sequence may have 0, 1, 2, 3, or 4 bases within the seed sequence that differ from the identified siRNA but are identical to the miRNA seed sequence. The mismatched nucleotides may be interspersed or contiguous. In an embodiment, the mismatches are located within nucleotides 1 through 9. In another embodiment, the mismatches are located within nucleotides 2 through 8. In still another embodiment, the mismatches are located within nucleotides 5 through 8. Depending on the number of nucleotides in the seed sequence, nucleotides 9 and on or nucleotides 10 and on of the aiRNA nucleotide sequence of the invention may be identical to the corresponding nucleotides of the identified siRNA. Accordingly, following the seed sequence of the miRNA, the rest of the aiRNA nucleotide sequence of the invention is identical to the identified siRNA. In an embodiment where the seed sequence consists of nucleotides 2 through 8, nucleotides 1 and 9 and on of the aiRNA nucleotide sequence may be identical to the corresponding nucleotides of the identified siRNA. In an embodiment where the seed sequence consists of nucleotides 1 through 9, nucleotides 10 and on of the aiRNA nucleotide sequence may be identical to the corresponding nucleotides of the identified siRNA. In an embodiment where the seed sequence consists of nucleotides 2 through 9, nucleotides 1 and 10 and on of the aiRNA nucleotide sequence may be identical to the corresponding nucleotides of the identified siRNA. In an embodiment where the seed sequence consists of nucleotides 1 through 8, nucleotides 9 and on of the aiRNA nucleotide sequence may be identical to the corresponding nucleotides of the identified siRNA.

An aiRNA nucleotide sequence of the invention is capable of specifically hybridizing to at least two target nucleic acids. As used herein, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizing" and "complementary" are terms which are used to indicate a sufficient degree of complementarity or precise pairing such that stable and specific binding occurs between the nucleotide sequence and the target nucleic acid. It is understood in the art that the sequence of an aiRNA nucleotide sequence of the invention need not be 100% complementary to that of its target nucleic acid to be specifically hybridizable. A nucleotide sequence is specifically hybridizable when binding of the nucleotide sequence to the target nucleic acid interferes with the normal function of the target nucleic acid to cause a loss of expression or function, and there is a sufficient degree of complementarity to avoid non-specific binding of the nucleotide sequence to non-target nucleic acids under conditions in which specific binding is desired, i.e., under physiological conditions in the case of in vivo assays or therapeutic treatment, and in the case of in vitro assays, under conditions in which the assays are performed.

In some embodiments, an aiRNA nucleotide sequence of the invention comprises a sequence selected from the group consisting of SEQ ID NO:6, SEQ ID NO:7, SEQ ID NO:8, nucleotides 37-57 of SEQ ID NO:13, and nucleotides 36-56 of SEQ ID NO:15. In other embodiments, an aiRNA nucleotide sequence of the inventions consists of a sequence selected from the group consisting of SEQ ID NO:6, SEQ ID NO:7, SEQ ID NO:8, nucleotides 37-57 of SEQ ID NO:13, and nucleotides 36-56 of SEQ ID NO:15. In certain embodiments, an aiRNA nucleotide sequence of the invention is a variant of a sequence selected from the group consisting of SEQ ID NO:6, SEQ ID NO:7, SEQ ID NO:8, nucleotides 37-57 of SEQ ID NO:13, and nucleotides 36-56 of SEQ ID NO:15, wherein the variant comprises at least 18 contiguous nucleotides of a sequence selected from the group consisting of SEQ ID NO:6, SEQ ID NO:7, SEQ ID NO:8, nucleotides 37-57 of SEQ ID NO:13, and nucleotides 36-56 of SEQ ID NO:15, provided the seed sequence is included, and functions substantially similar to an aiRNA nucleotide sequence comprising a sequence selected from the group consisting of SEQ ID NO:6, SEQ ID NO:7, SEQ ID NO:8, nucleotides 37-57 of SEQ ID NO:13, and nucleotides 36-56 of SEQ ID NO:15. For instance, an aiRNA nucleotide sequence of the invention may encompass at least 19, 20, 21, or 22 contiguous nucleotides of a sequence selected from the group consisting of SEQ ID NO:6, SEQ ID NO:7, SEQ ID NO:8, nucleotides 37-57 of SEQ ID NO:13, and nucleotides 36-56 of SEQ ID NO:15. In a specific embodiment, an aiRNA nucleotide sequence may comprise a sequence selected from the group consisting of SEQ ID NO:8, nucleotides 37-57 of SEQ ID NO:13, and nucleotides 36-56 of SEQ ID NO:15. In another specific embodiment, an aiRNA nucleotide sequence may consist of a sequence selected from the group consisting of SEQ ID NO:8, nucleotides 37-57 of SEQ ID NO:13, and nucleotides 36-56 of SEQ ID NO:15.

In an aspect, a nucleic acid construct of the invention comprises an aiRNA nucleotide sequence. A nucleic acid construct may be single stranded, double stranded, or a combination thereof. In some embodiments, a nucleic acid construct is double stranded. In other embodiments, a nucleic acid construct is single stranded. In yet other embodiments, a nucleic acid construct is a combination of single stranded and double stranded.

A nucleic acid construct of the invention may comprise ribonucleic acid (RNA), deoxyribonucleic acid (DNA), or a combination of RNA and DNA. In an exemplary embodiment, a nucleic acid construct may comprise DNA that codes for the RNA. Additionally, a nucleic acid construct may comprise modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). Alternatively, a nucleic acid construct may be a nucleotide mimic. Examples of nucleotide mimics include locked nucleic acids (LNA), peptide nucleic acids (PNA), and phosphorodiamidate morpholino oligomers (PMO).

In an aspect, the nucleic acid construct may comprise a short hairpin RNA (shRNA) comprising an aiRNA nucleotide sequence of the invention. In general, a shRNA is an RNA molecule comprising at least two complementary portions that are hybridized or are capable of hybridizing to form a double-stranded structure sufficiently long to mediate RNA interference (as described above), and at least one single-stranded portion that forms a loop connecting the regions of the shRNA that form the duplex. The structure may also be called a stem-loop structure, with the stem being the duplex portion. In some embodiments, the duplex portion of the structure may be completely complementary, such that no mismatches or bulges exist in the duplex region of the shRNA. In other embodiments, the duplex portion of the structure may be substantially complementary, such that one or more mismatches and/or bulges may exist in the duplex portion of the shRNA. The loop of the structure may be from about 1 to about 20 nucleotides in length, preferably from about 4 to about 10 about nucleotides in length, and more preferably from about 6 to about 9 nucleotides in length. The loop may be located at either the 5' or 3' end of the region that is complementary to the target transcript (i.e., the antisense portion of the shRNA). Exemplary shRNA molecules are depicted in FIG. 8.

The shRNA may further comprise an overhang on the 5' or 3' end. The optional overhang may be from about 1 to about 20 nucleotides in length, and more preferably from about 2 to about 15 nucleotides in length. In some embodiments, the overhang may comprise one or more U residues, e.g., between about 1 and about 5 U residues. In some embodiments, the 5' end of the shRNA may have a phosphate group, while in other embodiments it may not. In other embodiments, the 3' end of the shRNA may have a hydroxyl group, while in other embodiments it may not. In general, shRNAs are processed into aiRNAs by the conserved cellular RNAi machinery. Thus, shRNAs are precursors of aiRNAs and are similarly capable of inhibiting expression of a target transcript that is complementary of a portion of the shRNA (i.e., the antisense portion of the shRNA). Those of skill in the art are familiar with the available resources (as detailed above) for the design and synthesis of shRNAs. An exemplary example a shRNA is presented in FIG. 8 and Example 6.

In still other embodiments, the nucleic acid construct may be an RNA interference (RNAi) RNAi expression vector. Typically, an RNAi expression vector may be used for intracellular (in vivo) synthesis of RNAi agents, such as miRNAs, siRNAs, aiRNAs or shRNAs. In one embodiment, two separate, complementary aiRNA strands may be transcribed using a single vector containing two promoters, each of which directs transcription of a single aiRNA strand (i.e., each promoter is operably linked to a template for the aiRNA so that transcription may occur). The two promoters may be in the same orientation, in which case each is operably linked to a template for one of the complementary aiRNA strands. Alternatively, the two promoters may be in opposite orientations, flanking a single template so that transcription for the promoters results in synthesis of two complementary aiRNA strands. In another embodiment, the RNAi expression vector may contain a promoter that drives transcription of a single RNA molecule comprising two complementary regions, such that the transcript forms a shRNA.

Generally speaking, the promoters utilized to direct in vivo expression of the one or more aiRNA or shRNA transcription units may be promoters for RNA polymerase III (Pol III). Certain Pol III promoters, such as U6 or H1 promoters, do not require cis-acting regulatory elements within the transcribed region, and thus, are preferred in certain embodiments. In other embodiments, promoters for Pol II may be used to drive expression of the one or more aiRNA or shRNA transcription units. In some embodiments, tissue-specific, cell-specific, or inducible Pol II promoters may be used.

A construct that provides a template for the synthesis of aiRNA or shRNA may be produced using standard recombinant DNA methods and inserted into any of a wide variety of different vectors suitable for expression in eukaryotic cells. Guidance may be found in Current Protocols in Molecular Biology (Ausubel et al., John Wiley & Sons, New York, 2003) or Molecular Cloning: A Laboratory Manual (Sambrook & Russell, Cold Spring Harbor Press, Cold Spring Harbor, N.Y., 3rd edition, 2001). Those of skill in the art also appreciate that vectors may comprise additional regulatory sequences (e.g., termination sequence, translational control sequence, etc.), as well as selectable marker sequences. DNA plasmids are known in the art, including those based on pBR322, PUC, and so forth. Since many expression vectors already contain a suitable promoter or promoters, it may only be necessary to insert the nucleic acid sequence that encodes the RNAi agent of interest at an appropriate location with respect to the promoter(s). Viral vectors may also be used to provide intracellular expression of RNAi agents. Suitable viral vectors include retroviral vectors, lentiviral vectors, adenoviral vectors, adeno-associated virus vectors, herpes virus vectors, and so forth. In preferred embodiments, the RNAi expression vector is a shRNA lentiviral-based vector or lentiviral particle.

Nucleic acid sequences of the invention may be obtained using a variety of different techniques known in the art. The nucleotide sequences, as well as homologous sequences, may be isolated using standard techniques, purchased or obtained from a depository. Once the nucleotide sequence is obtained, it may be amplified for use in a variety of applications, using methods known in the art. The aiRNA may be enzymatically synthesized in vitro using methods well known to those of skill in the art. Alternatively, the siRNA may be chemically synthesized using oligonucleotide synthesis techniques that are well known in the art.

(c) Measuring Expression

In an aspect, the expression of at least two target nucleic acids may be measured. Methods of measuring the expression of nucleic acids are known in the art. Expression of at least two target nucleic acids may be measured directly by measuring nucleic acid expression or indirectly by measuring protein expression or target nucleic acid function. For example, expression of at least two target nucleic acids may be measured by cell assays specific to the target nucleic acid, or protein thereof, function. Methods of measuring nucleic acid and protein expression are described in detail below.

In an embodiment, a nucleic acid construct of the invention comprises an aiRNA nucleotide sequence capable of disrupting expression of at least two target nucleic acids in a cell. Disruption in expression of at least two target nucleic acids indicates hybridization of the aiRNA nucleotide sequence to the at least two target nucleic acids. As used herein, "disrupting expression of at least two target nucleic acids" may be used to describe any decrease in the expression level of at least two target nucleic acids, or proteins translated from the at least two target nucleic acids, when compared to a level of expression of the at least two target nucleic acids in a cell that was not treated with a nucleic acid construct of the invention. In an exemplary embodiment, a nucleic acid construct of the invention comprises an aiRNA nucleotide sequence capable of disrupting the expression of a nucleic acid encoding AKT1 and capable of disrupting the expression of nucleic acids regulated by miR-200a. Non-limiting examples of nucleic acids regulated by miR-200a may include ACOT7, ACTA1, ARPC5, ATOH8, C22orf23, CBX1, CDK6, DCTN3, DKK1, DPY19L1, DR1, DTX3, EVI5L, FAM158A, FAM220A, FAM35B, FAM72B, FLJ32255, GEM, GNB1L, HINT3, HMOX1, HOXC13, HS6ST2, ITGB3, KCTD20, KIDINS220, LBR, LOC100130331, LOC100507032, LOC100653106, LOC100653136, LOC100653311, LOC729852, LOXL3, LRRC8B, MAP2K4, MAP3K3, NRP1, NUP43, PDGFA, PDHA1, PDXP, PEX12, PIF1, PORCN, PPP3CC, PPT2, PPT2-EGFL8, RNF5P1, SERPINE1, SLC16A3, SLC30A1, SLC35D1, SLC39A10, SMARCD3, SNRPB2, SRM, TMEM158, TRMT112, TSPAN12, TST, TUBB8, UBASH3B, UPRT, WHAMM, WIPI1, YWHAG, ZEB1, and ZEB2.

In an embodiment, an aiRNA nucleotide sequence of the invention reduces expression of the target nucleic acids by greater than 25%. For example, an aiRNA nucleotide sequence of the invention reduces expression of the target nucleic acids by greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, or 100%. The reduction in expression may be of varying degrees for the target nucleic acids targeted by an aiRNA nucleotide sequence of the invention.

In certain embodiments, an aiRNA nucleotide sequence of the invention disrupts the expression of greater than 50% of the target nucleic acids regulated by the miRNA of the aiRNA nucleotide sequence. For example, an aiRNA nucleotide sequence of the invention disrupts the expression of greater than 50%, greater than 55%, greater than 60%, greater than 65%, greater than 70%, greater than 75%, greater than 80%, greater than 85%, greater than 90%, greater than 95%, or 100% of the target nucleic acids regulated by the miRNA of the aiRNA nucleotide sequence. In a specific embodiment, an aiRNA nucleotide sequence of the invention disrupts the expression of greater than 75% of the target nucleic acids regulated by the miRNA of the aiRNA nucleotide sequence.

(i) Methods for Assessing an Amount of Nucleic Acid Expression

Methods for assessing an amount of nucleic acid expression in cells are well known in the art, and all suitable methods for assessing an amount of nucleic acid expression known to one of skill in the art are contemplated within the scope of the invention. The term "amount of nucleic acid expression" or "level of nucleic acid expression" as used herein refers to a measurable level of expression of the nucleic acids, such as, without limitation, the level of messenger RNA (mRNA) transcript expressed or a specific variant or other portion of the mRNA, the enzymatic or other activities of the nucleic acids, and the level of a specific metabolite. The term "nucleic acid" includes DNA and RNA and can be either double stranded or single stranded. Non-limiting examples of suitable methods to assess an amount of nucleic acid expression may include arrays, such as microarrays, PCR, such as RT-PCR (including quantitative RT-PCR), nuclease protection assays and Northern blot analyses. In a specific embodiment, determining the amount of expression of a target nucleic acid comprises, in part, measuring the level of target nucleic acid mRNA expression.

In one embodiment, the amount of nucleic acid expression may be determined by using an array, such as a microarray. Methods of using a nucleic acid microarray are well and widely known in the art. For example, a nucleic acid probe that is complementary or hybridizable to an expression product of a target gene may be used in the array. The term "hybridize" or "hybridizable" refers to the sequence specific non-covalent binding interaction with a complementary nucleic acid. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. The term "probe" as used herein refers to a nucleic acid sequence that will hybridize to a nucleic acid target sequence. In one example, the probe hybridizes to an RNA product of the nucleic acid or a nucleic acid sequence complementary thereof. The length of probe depends on the hybridization conditions and the sequences of the probe and nucleic acid target sequence. In one embodiment, the probe is at least 8, 10, 15, 20, 25, 50, 75, 100, 150, 200, 250, 400, 500 or more nucleotides in length.

In another embodiment, the amount of nucleic acid expression may be determined using PCR. Methods of PCR are well and widely known in the art, and may include quantitative PCR, semi-quantitative PCR, multiplex PCR, or any combination thereof. Specifically, the amount of nucleic acid expression may be determined using quantitative RT-PCR. Methods of performing quantitative RT-PCR are common in the art. In such an embodiment, the primers used for quantitative RT-PCR may comprise a forward and reverse primer for a target gene. The term "primer" as used herein refers to a nucleic acid sequence, whether occurring naturally as in a purified restriction digest or produced synthetically, which is capable of acting as a point of synthesis when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less or more. The factors involved in determining the appropriate length of primer are readily known to one of ordinary skill in the art.

The amount of nucleic acid expression may be measured by measuring an entire mRNA transcript for a nucleic acid sequence, or measuring a portion of the mRNA transcript for a nucleic acid sequence. For instance, if a nucleic acid array is utilized to measure the amount of mRNA expression, the array may comprise a probe for a portion of the mRNA of the nucleic acid sequence of interest, or the array may comprise a probe for the full mRNA of the nucleic acid sequence of interest. Similarly, in a PCR reaction, the primers may be designed to amplify the entire cDNA sequence of the nucleic acid sequence of interest, or a portion of the cDNA sequence. One of skill in the art will recognize that there is more than one set of primers that may be used to amplify either the entire cDNA or a portion of the cDNA for a nucleic acid sequence of interest. Methods of designing primers are known in the art. Methods of extracting RNA from a biological sample are known in the art.

The level of expression may or may not be normalized to the level of a control nucleic acid. Such a control nucleic acid should not specifically hybridize with an aiRNA nucleotide sequence of the invention. This allows comparisons between assays that are performed on different occasions.

(ii) Methods for Assessing an Amount of Protein Expression

Methods for assessing an amount of protein expression are well known in the art, and all suitable methods for assessing an amount of protein expression known to one of skill in the art are contemplated within the scope of the invention. Non-limiting examples of suitable methods to assess an amount of protein expression may include epitope binding agent-based methods and mass spectrometry based methods.

In some embodiments, the method to assess an amount of protein expression is mass spectrometry. By exploiting the intrinsic properties of mass and charge, mass spectrometry (MS) can resolve and confidently identify a wide variety of complex compounds, including proteins. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). In accordance with the present invention, one can use mass spectrometry to look for the level of protein encoded from a target nucleic acid of the invention.

In some embodiments, the method to assess an amount of protein expression is an epitope binding agent-based method. As used herein, the term "epitope binding agent" refers to an antibody, an aptamer, a nucleic acid, an oligonucleic acid, an amino acid, a peptide, a polypeptide, a protein, a lipid, a metabolite, a small molecule, or a fragment thereof that recognizes and is capable of binding to a target gene protein. Nucleic acids may include RNA, DNA, and naturally occurring or synthetically created derivative.

As used herein, the term "antibody" generally means a polypeptide or protein that recognizes and can bind to an epitope of an antigen. An antibody, as used herein, may be a complete antibody as understood in the art, i.e., consisting of two heavy chains and two light chains, or may be any antibody-like molecule that has an antigen binding region, and includes, but is not limited to, antibody fragments such as Fab', Fab, F(ab')2, single domain antibodies, Fv, and single chain Fv. The term antibody also refers to a polyclonal antibody, a monoclonal antibody, a chimeric antibody and a humanized antibody. The techniques for preparing and using various antibody-based constructs and fragments are well known in the art. Means for preparing and characterizing antibodies are also well known in the art (See, e.g. Antibodies: A Laboratory Manual, Cold Spring Harbor Laboratory, 1988; herein incorporated by reference in its entirety).

As used herein, the term "aptamer" refers to a polynucleotide, generally a RNA or DNA that has a useful biological activity in terms of biochemical activity, molecular recognition or binding attributes. Usually, an aptamer has a molecular activity such as binging to a target molecule at a specific epitope (region). It is generally accepted that an aptamer, which is specific in it binding to a polypeptide, may be synthesized and/or identified by in vitro evolution methods. Means for preparing and characterizing aptamers, including by in vitro evolution methods, are well known in the art (See, e.g. U.S. Pat. No. 7,939,313; herein incorporated by reference in its entirety).

In general, an epitope binding agent-based method of assessing an amount of protein expression comprises contacting a sample comprising a polypeptide with an epitope binding agent specific for the polypeptide under conditions effective to allow for formation of a complex between the epitope binding agent and the polypeptide. Epitope binding agent-based methods may occur in solution, or the epitope binding agent or sample may be immobilized on a solid surface. Non-limiting examples of suitable surfaces include microtitre plates, test tubes, beads, resins, and other polymers.

An epitope binding agent may be attached to the substrate in a wide variety of ways, as will be appreciated by those in the art. The epitope binding agent may either be synthesized first, with subsequent attachment to the substrate, or may be directly synthesized on the substrate. The substrate and the epitope binding agent may be derivatized with chemical functional groups for subsequent attachment of the two. For example, the substrate may be derivatized with a chemical functional group including, but not limited to, amino groups, carboxyl groups, oxo groups or thiol groups. Using these functional groups, the epitope binding agent may be attached directly using the functional groups or indirectly using linkers.

The epitope binding agent may also be attached to the substrate non-covalently. For example, a biotinylated epitope binding agent may be prepared, which may bind to surfaces covalently coated with streptavidin, resulting in attachment. Alternatively, an epitope binding agent may be synthesized on the surface using techniques such as photopolymerization and photolithography. Additional methods of attaching epitope binding agents to solid surfaces and methods of synthesizing biomolecules on substrates are well known in the art, i.e. VLSIPS technology from Affymetrix (e.g., see U.S. Pat. No. 6,566,495, and Rockett and Dix, Xenobiotica 30(2):155-177, both of which are hereby incorporated by reference in their entirety).

Contacting the sample with an epitope binding agent under effective conditions for a period of time sufficient to allow formation of a complex generally involves adding the epitope binding agent composition to the sample and incubating the mixture for a period of time long enough for the epitope binding agent to bind to any antigen present. After this time, the complex will be washed and the complex may be detected by any method well known in the art. Methods of detecting the epitope binding agent-polypeptide complex are generally based on the detection of a label or marker. The term "label", as used herein, refers to any substance attached to an epitope binding agent, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, $Ni^{2+}$, Flag tags, myc tags, heavy metals, and enzymes (including alkaline phosphatase, peroxidase, and luciferase). Methods of detecting an epitope binding agent-polypeptide complex based on the detection of a label or marker are well known in the art.

In some embodiments, an epitope binding agent-based method is an immunoassay. Immunoassays can be run in a number of different formats. Generally speaking, immunoassays can be divided into two categories: competitive immunoassays and non-competitive immunoassays. In a competitive immunoassay, an unlabeled analyte in a sample competes with labeled analyte to bind an antibody. Unbound analyte is washed away and the bound analyte is measured. In a non-competitive immunoassay, the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled.) Suitable labels are described above.

In some embodiments, the epitope binding agent-based method is an ELISA. In other embodiments, the epitope binding agent-based method is a radioimmunoassay. In still other embodiments, the epitope binding agent-based method is an immunoblot or Western blot. In alternative embodiments, the epitope binding agent-based method is an array. In another embodiment, the epitope binding agent-based method is flow cytometry. In different embodiments, the epitope binding agent-based method is immunohistochemistry (IHC). IHC uses an antibody to detect and quantify antigens in intact tissue samples. The tissue samples may be fresh-frozen and/or formalin-fixed, paraffin-embedded (or plastic-embedded) tissue blocks prepared for study by IHC. Methods of preparing tissue block for study by IHC, as well as methods of performing IHC are well known in the art.

(iii) Cell Assays

In an embodiment, expression of at least two target nucleic acids may be measured by cell assays specific to the target nucleic acid, or protein thereof, function. Accordingly, based on the target nucleic acids, a cell assay may be used to determine if the expression is disrupted. For example, cell migration rate, cell motility, cell proliferation rate, cell invasion, and/or cellular morphology may be used to measure expression of at least two target nucleic acids. Using a cell assay specific to the function of the target nucleic acid may indirectly indicate a disruption in expression of a target nucleic acid.

II. Pharmaceutical Composition

In another aspect of the invention, a nucleic acid construct of the invention may be incorporated into pharmaceutical compositions suitable for administration. A pharmaceutical composition of the invention may be used to disrupt the expression of at least two target nucleic acids expressed in a cell. For instance, a pharmaceutical composition of the invention may be used to disrupt the expression of 2, 3, 4, 5, 6, 7, 8, 9, 10 or more nucleic acids expressed in a cell. Additionally, a pharmaceutical composition of the invention may be used to disrupt the expression of 10, 15, 20, 25, 30, 35, 40, 45, 50, 55, 60, 65, 70, 75, 80, 85, 90, 95, 100 or more nucleic acids expressed in a cell. A skilled artisan will appreciate that pharmaceutical compositions may be administered to treat a disease, to prevent a disease, or to promote good health. As such, a pharmaceutical composition of the invention may be used to disrupt expression of any nucleic acid sequence expressed in a cell, such that disrupted expression leads to measurable and beneficial effects for the subject administered the composition (i.e. significant efficacy).

In some embodiments, a pharmaceutical composition of the invention is used to disrupt the expression of at least two target nucleic acids expressed in a cell. In a preferred embodiment, a pharmaceutical composition of the invention is used to disrupt the expression of a nucleic acid sequence encoding AKT1 and nucleic acids regulated by miR-200a. Non-limiting examples of nucleic acids regulated by miR-200a may be found in Table 1.

A pharmaceutical composition of the invention may also comprise one or more nontoxic pharmaceutically acceptable carriers, adjuvants, excipients, and vehicles as desired. As used herein, the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with nanoparticles of the invention, use thereof in the compositions is contemplated. Supplementary active compounds may also be incorporated into the compositions.

A pharmaceutical composition of the invention may be formulated to be compatible with its intended route of administration. Suitable routes of administration include parenteral, oral, pulmonary, transdermal, transmucosal, and rectal administration. The term parenteral, as used herein, includes subcutaneous, intravenous, intramuscular, intrathecal, or intrasternal injection, or infusion techniques.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH may be adjusted with acids or bases, such as hydrochloric acid or sodium hydroxide. The parenteral preparation may be enclosed in ampoules, disposable syringes or multiple dose vials made of glass or plastic.

Oral compositions generally may include an inert diluent or an edible carrier. Oral compositions may be enclosed in gelatin capsules or compressed into tablets. For the purpose of oral therapeutic administration, the active compound may be incorporated with excipients and used in the form of tablets, troches, or capsules. Oral compositions may also be prepared using a fluid carrier for use as a mouthwash, wherein the compound in the fluid carrier is applied orally and swished and expectorated or swallowed. Pharmaceutically compatible binding agents and/or adjuvant materials may be included as part of the composition. The tablets, pills, capsules, troches, and the like, may contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressured container or dispenser which contains a suitable propellant, e.g., a gas such as carbon dioxide, or a nebulizer.

In preferred embodiments, a pharmaceutical composition of the invention is formulated to be compatible with parenteral administration. For instance, pharmaceutical compositions suitable for injectable use may include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.), or phosphate buffered saline (PBS). In exemplary embodiments, a pharmaceutical composition of the invention is formulated with phosphate buffered saline (PBS).

In all cases, a composition may be sterile and may be fluid to the extent that easy syringeability exists. A composition may be stable under the conditions of manufacture and storage, and may be preserved against the contaminating action of microorganisms such as bacteria and fungi. The carrier may be a solvent or dispersion medium containing, for example, water, ethanol, polyol (for example, glycerol, propylene glycol, and liquid polyetheylene glycol, and the like), and suitable mixtures thereof. The proper fluidity may be maintained, for example, by the use of a coating such as lecithin, by the maintenance of the required particle size in the case of dispersion, and by the use of surfactants. Prevention of the action of microorganisms may be achieved by various antibacterial and antifungal agents, for example, parabens, chlorobutanol, phenol, ascorbic acid, thimerosal, and the like. In many cases, it may be preferable to include isotonic agents, for example, sugars, polyalcohols such as mannitol, sorbitol, or sodium chloride, in the composition. Prolonged absorption of the injectable compositions may be brought about by including in the composition an agent which delays absorption, for example, aluminum monostearate and gelatin.

Sterile injectable solutions may be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Systemic administration may also be by transmucosal or transdermal means. For transmucosal or transdermal administration, penetrants appropriate to the barrier to be permeated are used in the formulation. Such penetrants are generally known in the art, and may include, for example, for transmucosal administration, detergents, bile salts, and fusidic acid derivatives. Transmucosal administration may be accomplished through the use of nasal sprays or suppositories. For transdermal administration, the active compounds are formulated into ointments, salves, gels, or creams as generally known in the art. The compounds may also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylactic acid. Methods for preparation of such formulations will be apparent to those skilled in the art. These may be prepared according to methods known to those skilled in the art, for example, as described in U.S. Pat. No. 4,522,811.

Additional formulations of pharmaceutical compositions may be in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980). Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

One of skill in the art will recognize that the concentration of a nucleic acid construct of the invention in a pharmaceutical composition can and will vary depending in part on the route of administration, the subject, and the reason for the administration, and may be determined experimentally. Methods of experimentally determining the concentration of an active agent such as nanoparticles of the invention in a pharmaceutical composition are known in the art. In general, a pharmaceutical composition may be formulated to comprise about 0.1 nM to about 50 µM of a nucleic acid construct of the invention. In some embodiments, a pharmaceutical composition may be formulated to comprise about 0.1 nM to about 1.0 nM of a nucleic acid construct of the invention. In other embodiments, a pharmaceutical composition may be formulated to comprise about 1 nM to about 10 nM of a nucleic acid construct of the invention. In other embodiments, a pharmaceutical composition may be formulated to comprise about 1 nM to about 100 nM of a nucleic acid construct of the invention. In other embodiments, a pharmaceutical composition may be formulated to comprise about 1 nM to about 200 nM of a nucleic acid construct of the invention. In other embodiments, a pharmaceutical composition may be formulated to comprise about 1 nM to about 50 nM of a nucleic acid construct of the invention. In other embodiments, a pharmaceutical composition may be formulated to comprise about 10 nM to about 100 nM of a nucleic acid construct of the invention. In other embodiments, a pharmaceutical composition may be formulated to comprise about 10 nM to about 200 nM of a nucleic acid construct of the invention. In other embodiments, a pharmaceutical composition may be formulated to comprise about 50 nM to about 100 nM of a nucleic acid construct of the invention. In other embodiments, a pharmaceutical composition may be formulated to comprise about 50 nM to about 200 nM of a nucleic acid construct of the invention. In other embodiments, a pharmaceutical composition may be formulated to comprise about 100 nM to about 200 nM of a nucleic acid construct of the invention. In other embodiments, a pharmaceutical composition may be formulated to comprise about 150 nM to about 200 nM of a nucleic acid construct of the invention. In other embodiments, a pharmaceutical composition may be formulated to comprise about 200 nM to about 1000 nM of a nucleic acid construct of the invention. In other embodiments, a pharmaceutical composition may be formulated to comprise about 500 nM to about 1000 nM of a nucleic acid construct of the invention. In other embodiments, a pharmaceutical composition may be formulated to comprise about 1 µM to about 50 µM of a nucleic acid construct of the invention.

A pharmaceutical composition may also be formulated to comprise about 30, 40, 50, 60, 70, 80, 90, 100, 150, 200, 250, 300, 350, 400, 450, 500, 550, 600, 650, or about 700 µg/ml or more of a nucleic acid construct of the invention. In some embodiments, a pharmaceutical composition is formulated to comprise 30, 35, 40, 45, 50, 55, 60, 65, 70, 75, 80, 85, 90, 95, or about 100 µg/ml of a nucleic acid construct of the invention. In other embodiments, a pharmaceutical composition is formulated to comprise 100, 110, 120, 130, 140, 150, 160, 170, 180, 190, 200, 210, 220, 230, 240, 250, 260, 270, 280, 290, or about 300 µg/ml of a nucleic acid construct of the invention. In yet other embodiments, a pharmaceutical composition is formulated to comprise 300, 310, 320, 330, 340, 350, 360, 370, 380, 390, 400, 410, 420, 430, 440, 450, 460, 470, 480, 490, or about 500 µg/ml of a nucleic acid construct of the invention. In yet other embodiments, a pharmaceutical composition is formulated to comprise 500, 510, 520, 530, 540, 550, 560, 570, 580, 590, 600, 610, 620, 630, 640, 650, 660, 670, 680, 690, or about 700 µg/ml or more of a nucleic acid construct of the invention.

III. Method of Treatment

In another aspect, the invention encompasses a method for using a nucleic acid construct of the invention to express the aiRNA nucleotide sequence in a cell. In still another aspect, the invention encompasses a method for using a nucleic acid construct of the invention to transfect the aiRNA nucleotide sequence into the cytoplasm of a cell. In some embodiments, the cell is in vitro. In other embodiments, the cell is in vivo. Thus, the present invention also provides a method for using a nucleic acid construct of the invention to express the aiRNA nucleotide sequence in a cell in a subject in need thereof. Additionally, the present invention provides a method for using a nucleic acid construct of the invention to transfect the aiRNA nucleotide sequence into the cytoplasm of a cell in a subject in need thereof. Generally speaking, a method of the invention comprises contacting a cell with a nucleic acid construct of the invention under conditions suitable for expression of an aiRNA nucleotide sequence or under conditions suitable for transfection of an aiRNA nucleotide sequence. In embodiments where the cell is in vivo, a method of the invention typically comprises administering a pharmaceutical composition comprising a nucleic acid construct of the invention to a subject in need thereof. Suitable pharmaceutical compositions are described in Section II.

In another aspect, the invention encompasses a method for treating a condition in a subject. The method comprises administering to a subject in need thereof a therapeutically effective amount of a pharmaceutical composition comprising a nucleic acid construct. A nucleic acid construct of the invention is capable of efficiently expressing, or transfecting, the aiRNA nucleotide sequence of the nucleic acid construct in a cell of the subject.

In some embodiments, a nucleic acid construct of the invention comprises an aiRNA nucleotide sequence capable of regulating or inhibiting expression of at least target two nucleic acids expressed in a cell. By efficiently transfecting an aiRNA nucleotide sequence capable of regulating or inhibiting expression of at least two target nucleic acids expressed in a cell, a method of the invention may be used to treat any condition that can be treated by regulating or inhibiting the expression of at least two target nucleic acids expressed in a cell. In some preferred embodiments, the invention encompasses a method of administering a nucleic acid construct of the invention to a subject to treat a cancer in the subject.

The aiRNA nucleotide sequence and the nucleic acid construct may be as described in Section I. Pharmaceutical compositions comprising a nucleic acid construct of the invention may be as described in Section II. Methods of administering a nucleic acid construct of the invention, and methods of treating a condition are described below.

(a) Administration to a Subject in Need Thereof

In an aspect, the present invention encompasses administering a therapeutically effective amount of a pharmaceutical composition to a subject in need thereof. As used herein, the phrase "a subject in need thereof" refers to a subject in need of preventative or therapeutic treatment. A subject may be a rodent, a human, a livestock animal, a companion animal, or a zoological animal. In one embodiment, a subject may be a rodent, e.g., a mouse, a rat, a guinea pig, etc. In another embodiment, a subject may be a livestock animal. Non-limiting examples of suitable livestock animals may include pigs, cows, horses, goats, sheep, llamas and alpacas. In still another embodiment, a subject may be a companion animal. Non-limiting examples of companion animals may include pets such as dogs, cats, rabbits, and birds. In yet another embodiment, a subject may be a zoological animal. As used herein, a "zoological animal" refers to an animal that may be found in a zoo. Such animals may include non-human primates, large cats, wolves, and bears. In a preferred embodiment, a subject is a mouse. In another preferred embodiment, a subject is a human.

As described in Section II, a pharmaceutical composition of the invention is formulated to be compatible with its intended route of administration. Suitable routes of administration include parenteral, oral, pulmonary, transdermal, transmucosal, and rectal administration. In preferred embodiments, a pharmaceutical composition of the invention is administered by injection.

One of skill in the art will recognize that the amount and concentration of the composition administered to a subject will depend in part on the subject and the reason for the administration. Methods for determining optimal amounts are known in the art. In general, the concentration of a nucleic acid construct of the invention in a pharmaceutical composition may be as described in Section II.

Compositions of the invention are typically administered to a subject in need thereof in an amount sufficient to provide a benefit to the subject. This amount is defined as a "therapeutically effective amount." A therapeutically effective amount may be determined by the efficacy or potency of the particular composition, the disorder being treated, the duration or frequency of administration, the method of administration, and the size and condition of the subject, including that subject's particular treatment response. A therapeutically effective amount may be determined using methods known in the art, and may be determined experimentally, derived from therapeutically effective amounts determined in model animals such as the mouse, or a combination thereof. Additionally, the route of administration may be considered when determining the therapeutically effective amount. In determining therapeutically effective amounts, one skilled in the art may also consider the existence, nature, and extent of any adverse effects that accompany the administration of a particular compound in a particular subject.

When a pharmaceutical composition of the invention is administered to a subject by injection, a composition may be administered to the subject in a bolus in an amount of about 0.1 to about 10 mg/kg, or about 10 to about 50 mg/kg, or about 50 to about 100 mg/kg or more. A composition may also be administered by injecting more than one bolus into the subject over a period of time. For instance, a composition may be administered by injecting 1, 2, 3, 4, 5, 6, 7, 8, 9, 10 or more boluses into the subject. The boluses may be injected about every 1, 2, 3, 4, 5, 6, 7, 8, 9, 10, 11, or about every 12 hours, or they may be injected about every 1, 2, 3, 4, 5, 6, or about every 7 days. In preferred embodiments, boluses may be injected about every day.

(b) Treating Cancer

In preferred embodiments, a method of the invention is used to treat a neoplasm or cancer. The neoplasm may be malignant or benign, the cancer may be primary or metastatic; the neoplasm or cancer may be early stage or late stage. A cancer or a neoplasm may be treated by delivering a nucleic acid sequence to a cancer tumor in a subject. The cancer or neoplasm may be treated by slowing cancer cell growth or killing cancer cells.

In some embodiments, an aiRNA nucleotide sequence of a nucleic acid construct of the invention may treat a cancer or a neoplasm by delivering an aiRNA nucleotide sequence to a cancer cell in a subject in vivo. Non-limiting examples of neoplasms or cancers that may be treated with a method of the invention may include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sezary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-cell lymphoma (cutaneous), T-cell leukemia and lymphoma, testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood). In a preferred embodiment, a method of the invention is used to treat T-cell leukemia and lymphoma. In an exemplary embodiment, a method of the invention is used to treat Human T-Lymphotropic Virus-1 (HTLV-1) induced adult T-cell leukemia/lymphoma (ATLL).

In other embodiments, an aiRNA nucleotide sequence of a nucleic acid construct of the invention may be delivered to a cancer cell in vitro. For instance, an aiRNA nucleotide sequence of a nucleic acid construct of the invention may be delivered to a cancer cell line in vitro. A cancer cell may be a cancer cell line cultured in vitro. In some alternatives of the embodiments, a cancer cell line may be a primary cell line that is not yet described. Methods of preparing a primary cancer cell line utilize standard techniques known to individuals skilled in the art. In other alternatives, a cancer cell line may be an established cancer cell line. A cancer cell line may be adherent or non-adherent, or a cell line may be grown under conditions that encourage adherent, non-adherent or organotypic growth using standard techniques known to individuals skilled in the art. A cancer cell line may be contact inhibited or non-contact inhibited.

In some embodiments, the cancer cell line may be an established human cell line derived from a tumor. Non-limiting examples of cancer cell lines derived from a tumor may include the osteosarcoma cell lines 143B, CAL-72, G-292, HOS, KHOS, MG-63, Saos-2, and U-2 OS; the prostate cancer cell lines DU145, PC3 and Lncap; the breast cancer cell lines MCF-7, MDA-MB-438 and T47D; the myeloid leukemia cell line THP-1, the glioblastoma cell line U87; the neuroblastoma cell line SHSY5Y; the bone cancer cell line Saos-2; the colon cancer cell lines WiDr, COLO 320DM, HT29, DLD-1, COLO 205, COLO 201, HCT-15, SW620, LoVo, SW403, SW403, SW1116, SW1463, SW837, SW948, SW1417, GPC-16, HCT-8, HCT 116, NCI-H716, NCI-H747, NCI-H508, NCI-H498, COLO 320HSR, SNU-C2A, LS 180, LS 174T, MOLT-4, LS513, LS1034, LS411N, Hs 675.T, CO 88BV59-1, Co88BV59H21-2, Co88BV59H21-2V67-66, 1116-NS-19-9, TA 99, AS 33, TS 106, Caco-2, HT-29, SK-CO-1, SNU-C2B and SW480; B16-F10, RAW264.7, the F8 cell line, and the pancreatic carcinoma cell line Panc1. In a specific embodiment, the cell line may be HeLa cells or HCT116 cells.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction for the Examples

RNA interference (RNAi) is an RNA-guided gene silencing process within living cells that controls the expression of the targeted genes (Hannon 2002; Denli and Hannon 2003; Sontheimer 2005). There are two major types of small RNA molecules that are central to RNA interference, microRNAs (miRNAs) and small interfering RNAs (siRNAs).

miRNAs are a family of small non-coding RNA molecules (~22 nucleotides) that downregulate the expression of their gene targets (Miska 2005). Over two thousand human miRNAs have been identified to date (Kozomara and Griffiths-Jones 2011). Both computational and experimental studies indicate that thousands of human protein-coding genes are directly regulated by miRNAs (Lewis et al. 2005; Lim et al. 2005; Miranda et al. 2006). Thus, miRNAs function as master regulators for many important biological processes, such as cell growth, differentiation, apoptosis, viral infection and cancer development (Ambros 2004; Miska 2005; Calin and Croce 2006; Kent and Mendell 2006; Johnson et al. 2007).

Given the importance of miRNA-mediated gene regulation in disease biology, the diagnostic and therapeutic potential of miRNAs has been extensively explored in recent years. miRNAs are especially important in cancer development, as multiple miRNAs have been shown to be tumor suppressors or oncogenes (Croce 2009). To date, many studies have been published on using miRNAs as diagnostic and prognostic cancer biomarkers. In addition, clinical studies are underway to manipulate the expression level of miRNAs for the intervention of a variety of human diseases including cancer [reviewed in (Wurdinger and Costa 2007; Tong and Nemunaitis 2008)]. For example, introduction of tumor-suppressive miRNAs in human cancers may be an effective approach to suppress tumor growth (Kota et al. 2009; Rossi 2009; Valastyan et al. 2009).

For most miRNA-based therapeutic studies, naturally processed mature miRNAs are evaluated. One potential concern is that these natural miRNAs may not have the desired efficacy for functional gene regulation in therapeutic applications. In general, miRNA-mediated target suppression is relatively moderate as compared to siRNA-mediated gene knockdown. Although a single miRNA can simultaneously target many genes, only a limited number of cellular phenotypes may be observed. For example, miR-200a has a significant impact on cancer metastasis by suppressing the motility of cancer cells (Gregory et al. 2008; Park et al. 2008). However, miR-200a does not have any reported regulatory role on some other important cancer cell properties such as proliferation or cell death.

The major goal of our study is to engineer new potent small RNAs for RNAi-based therapy. To this end, we propose to improve the efficacy of disease-targeting miRNA by rational design of artificial interference RNA (termed aiRNA in our study). These aiRNA molecules were miRNA-siRNA chimeras, which were designed in silico based on natural miRNA as well as siRNA sequences. We hypothesized that, by simultaneously targeting genes from multiple functional categories that are related to the same disease, the therapeutic efficacy of an aiRNA can be greatly enhanced as compared to a single miRNA or siRNA. Specifically, we used human cancer as an example to test this new approach, and showed that an aiRNA designed based on miR-200a and AKT1 siRNA had enhanced functional efficacy by simultaneously suppressing both the motility and proliferation of cancer cells.

Example 1 aiRNAs and miRNAs Share Similar Targeting Characteristics

Our definition for artificial interference RNA (aiRNA) is as the following: an RNA molecule that is not present in nature, and has a similar sequence length to naturally processed mature miRNAs. By this definition, synthetic siRNAs can also be considered as a special form of aiRNA. An siRNA is typically a chemically synthesized 21-mer RNA duplex, with one strand having 100% sequence complementarity to a single intended mRNA target. siRNAs are widely used to knockdown the expression of their gene targets. Thus, the analysis of siRNAs will give us useful clues about the general properties of aiRNAs.

It has been shown in previous studies that introduction of siRNAs into the cells can trigger wide-spread off-target effects. Hundreds of unintended genes can be directly silenced by siRNA overexpression (Jackson et al. 2003; Birmingham et al. 2006; Jackson et al. 2006; Anderson et al. 2008). Seed region is defined as positions 2-8 of a miRNA or siRNA sequence. Similar to the seed pairing requirement in miRNA-mediated gene targeting, recent studies indicate that many siRNA off-targets have siRNA seed-pairing sites in the 3'-UTRs. In addition, bioinformatics analysis indicates that multiple targeting determinants outside of the seed match, such as local AU content and base composition at certain sequence positions, are also shared by both miRNAs and siRNAs. Thus, in general, siRNA off-targeting is very similar to gene expression suppression by natural miRNAs. These studies suggest that miRNAs and siRNAs enter identical or similar silencing complexes and mediate similar effects on their targets (Nielsen et al. 2007).

Given the high similarity between siRNA off-targeting and miRNA target regulation, it is reasonable to expect that an algorithm designed for miRNA target prediction should also be applicable to the prediction of genes targeted by aiRNAs (including siRNAs). To test this hypothesis, we analyzed the off-target signature of an siRNA targeting GAPDH. The siRNA off-targets were computationally predicted using MirTarget2, which is an algorithm developed in our previous study for miRNA target prediction (Wang 2008; Wang and El Naqa 2008). A recent independent study has demonstrated that MirTarget2 [data retrieved from miRDB (Wang 2008)] has superior performance over other common target prediction algorithms in comparative proteomic data analysis (Mestdagh et al. 2011). To experimentally validate MirTarget2 prediction result, the siRNA was overexpressed in HeLa cells and microarrays were performed to globally identify siRNA off-targets at the transcriptome level. As expected, the single intended target, GAPDH was silenced by the siRNA, with only 4% remaining mRNA level. Interestingly, among all siRNA off-targets predicted by MirTarget2, the majority were downregulated by at least 10% (i.e. less than 90% remaining expression, FIG. 1). Moreover, over one fifth of all predicted off-targets were downregulated by at least 30%. The level of off-target suppression is consistent with previous observations that siRNA off-targets are generally silenced at a more moderate level as compared to silencing of the intended targets (Jackson et al. 2003; Birmingham et al. 2006; Jackson et al.

2006; Anderson et al. 2008). In contrast to the wide-spread downregulation of predicted siRNA off-targets, less than 5% of all genes expressed in HeLa cells were downregulated by 30% or more (FIG. 1, $p=3.5E-17$ with $\chi^2$ test). Our data suggested that the targeting rules by aiRNAs (exemplified by a GAPDH siRNA) and natural miRNAs are similar, which opens a door to computationally design aiRNAs to mimic or even enhance the functionality of naturally processed miRNAs.

Example 2

Design of Multi-Functional aiRNAs by Mimicking Both miR-200a and AKT1 siRNA

Figure 2:
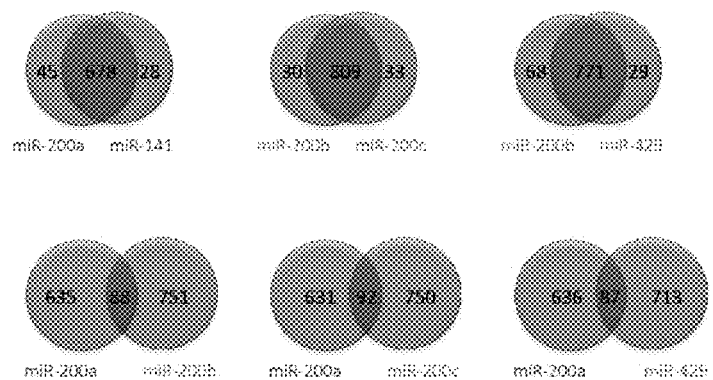
FIG. 2 depicts sequences and Venn diagrams of computational prediction of gene targets of the miR-200 family. (A) Sequences of five miRNAs in the miR-200 family. The miRNA sequences were aligned to miR-200a, and identical bases to miR-200a were represented by hyphen. The seed region of miR-200a is underlined. miR-200a (SEQ ID NO:1—UAACACUGUCUGGUAACGAUGU); miR-141 (SEQ ID NO:2—UAACACUGUCUGGUAAAGAUGG); miR-200b (SEQ ID NO:3—UAAUACUGCCUGGUAAUGAUGA); miR-200c (SEQ ID NO:4—UAAUACUGCCGGGUAAUGAUGGA); miR-429 (SEQ ID NO:5—UAACUCUGUCUGGUAAAACCGU) (B) Pair-wise comparison of gene sets targeted by different miR-200 family members, as predicted by MirTarget2.

We and others have previously shown that miRNA target specificity is determined by multiple sequence features, among which seed sequence match is the most critical determinant. The dominant role of seed match in miRNA target prediction was demonstrated here by comparing predicted target sets of miRNAs from the miR-200 family, which is known to suppress cancer cell motility by targeting multiple genes involved in epithelial-mesenchymal transition (EMT), leading to significantly reduced ability of cancer cells to migrate to distant sites to form metastatic lesions (Gregory et al. 2008; Park et al. 2008). There are five members in the miR-200 family. Among them, miR-200a and miR-141 share the same seed sequence, while miR-200b, miR-200c and miR-429 share a different seed sequence (FIG. 2A). For any pair of miR-200 members, the predicted target sets were almost identical if the seed sequence is shared by both miRNAs (miR-200a/miR-141, miR-200b/miR-200c or miR-200b/miR-429 as shown in FIG. 2B). In contrast, there was little overlap between predicted target sets if two miRNAs have distinct seed sequences (even resulting from a single base variation). Interestingly, differences in the 3' portion of the miRNA sequence were much less important than the seed region in target prediction. For example, miR-200b and miR-429 sequences are different by eight bases, yet the predicted targets sets for the two miRNAs were still highly similar (with >90% overlap) because both miRNAs share the same seed region.

Given the utmost importance of seed sequence in determining miRNA targets, we hypothesized that aiRNAs sharing the same seed sequence with miR-200a should also target a very similar set of genes, leading to functional suppression of tumor cell motility. These miR-200a-mimicking aiRNAs are termed as aiR-200a in our study. Furthermore, enhanced tumor suppressive functions could be achieved by rational design of the non-seed sequence of aiR-200a. Specifically, our design goal was to engineer novel aiRNAs that not only share miR-200a functions for suppressing tumor cell motility, but also bear new functions for suppressing tumor cell proliferation. By simultaneously suppressing both the motility and proliferation of tumor cells, aiR-200a was expected to have enhanced functions for tumor suppression as compared to naturally processed miR-200a.

The anti-proliferation function of aiR-200a was engineered by targeting a well-established oncogene, AKT1. AKT1 is not a predicted target of any miR-200 family member. AKT1 promotes the proliferation rate of cancer cells and overexpression of AKT1 has been observed in many human cancers (Bellacosa et al. 2005). By silencing AKT1, tumor growth can be greatly suppressed. Thus, AKT1 has been explored as an anti-cancer therapeutic target in many studies [reviewed in (Bellacosa et al. 2005)].

In our design algorithm for aiR-200a, the siRNA targeting mechanism was invoked to knock down AKT1. The most straightforward design would have been the selection of a potent AKT1 siRNA that shares the same seed sequence with miR-200a. However, no such siRNA could be designed because the AKT1 transcript sequence does not contain any miR-200a seed binding site. Thus, an alternative strategy was employed to mimic AKT1 siRNA. Interestingly, previous studies showed that siRNAs containing a few mismatched bases to the target binding sites could still potentially knock down their intended gene targets, similarly to perfectly matched siRNAs (Jackson et al. 2003; Jackson et al. 2006). Thus, AKT1-targeting aiR-200a could potentially be designed by introducing a few mismatched bases into an AKT1 siRNA. In this way, these aiRNAs may still silence AKT1 via RNAi-mediated transcript degradation despite the presence of base mismatches.

As the first step of aiR-200a design, we selected siRNAs to target AKT1. Design of AKT1-targeting siRNAs was performed using our recently developed tool, siOligo, which implemented a machine learning algorithm for selection of highly potent siRNAs (Wang et al. 2009). siOligo has been extensively validated experimentally for the design of hyperfunctional siRNAs, and it has been used for the design of most siRNA products by Ambion/Applied Biosystems. With siOligo, over one thousand candidate siRNAs targeting AKT1 were evaluated, and one hundred top-ranking siRNAs were selected based on their predicted knockdown efficiency. From these selected siRNAs, we then designed candidate aiR-200a sequences by replacing the seed region of the siRNA sequence with miR-200a seed sequence. aiR-200a sequences with the fewest number of mismatched bases to the corresponding siRNAs were retained. In this way, three aiR-200a RNAs were designed, with 2-3 mismatches in the seed region to the corresponding AKT1 siRNAs (FIG. 3A). Specifically, one aiR-200a RNA has two interspersed mismatches, while the other two have two and three contiguous mismatches, respectively.

By sharing the same seed region, aiR-200a RNAs and miR-200a were expected to target similar gene sets. To confirm this bioinformatically, MirTarget2 was employed for the prediction of genes targeted by miR-200a and aiR-200a, respectively, and the target sets were compared. As shown in FIG. 3B, the vast majority of miR-200a targets were also targets of all three aiR-200a RNAs, despite the fact that the 3' portions of aiR-200a and miR-200a were completely different. Specifically, 91%, 84% and 87% of all predicted miR-200a targets were predicted to be targeted by the three aiRNA-200a RNAs (aiRNA-200a-1, aiRNA-200a-3 and aiRNA-200a-3), respectively.

Example 3

Experimental Validation of Selected aiR-200a Targets

The in silico designed gene silencing capability of aiR-200a was evaluated experimentally. As the first step of functional validation, the suppression of three potential gene targets by aiR-200a was analyzed, including AKT1, ZEB1 and ZEB2. Among them, ZEB1 and ZEB2 are well-established miR-200a targets that promote cancer metastasis (Gregory et al. 2008; Park et al. 2008), both of which were predicted to be targeted by all three aiR-200a RNAs.

First, real-time RT-PCR was performed to assess gene knockdown at the mRNA level. As shown in FIG. 3C, all three aiR-200a RNAs were able to significantly suppress mRNA expression of both ZEB1 and ZEB2 by about 50%, a level comparable to that observed in miR-200a mediated target suppression. In contrast, none of the two AKT1 siRNAs were able to impact the expression of ZEB1 or ZEB2. On the other hand, both AKT1 siRNAs, but not miR-200a, were able to drastically silence the expression of AKT1 transcript by over 70%. As to the three aiR-200a RNAs, they behaved differently in AKT1 knockdown. One of them, aiR-200a-3 was able to knock down AKT1 transcript by about 60%, while the other two had insignificant impact on AKT1 knockdown. The divergent capabilities of AKT1 knockdown by different aiR-200a RNAs were also confirmed at the protein expression level. As shown in FIG. 3D, only aiR-200a-3, but not the other two aiRNAs, was able to suppress AKT1 protein expression to a level similar to that observed in siRNA-mediated AKT1 knockdown. Interestingly, aiR-200a-3 has two adjacent mismatched bases to AKT1 transcript. In contrast, the other two aiRNAs have either more mismatches or interspersed mismatches (FIG. 2A). In summary, aiR-200a-3 met our design goal of silencing both AKT1 and selected miR-200a targets. Thus, this aiRNA was further evaluated for global target downregulation at the transcriptome level.

Example 4 aiR-200a and miR-200a Targeted Similar Sets of Genes Globally

Figure 4:
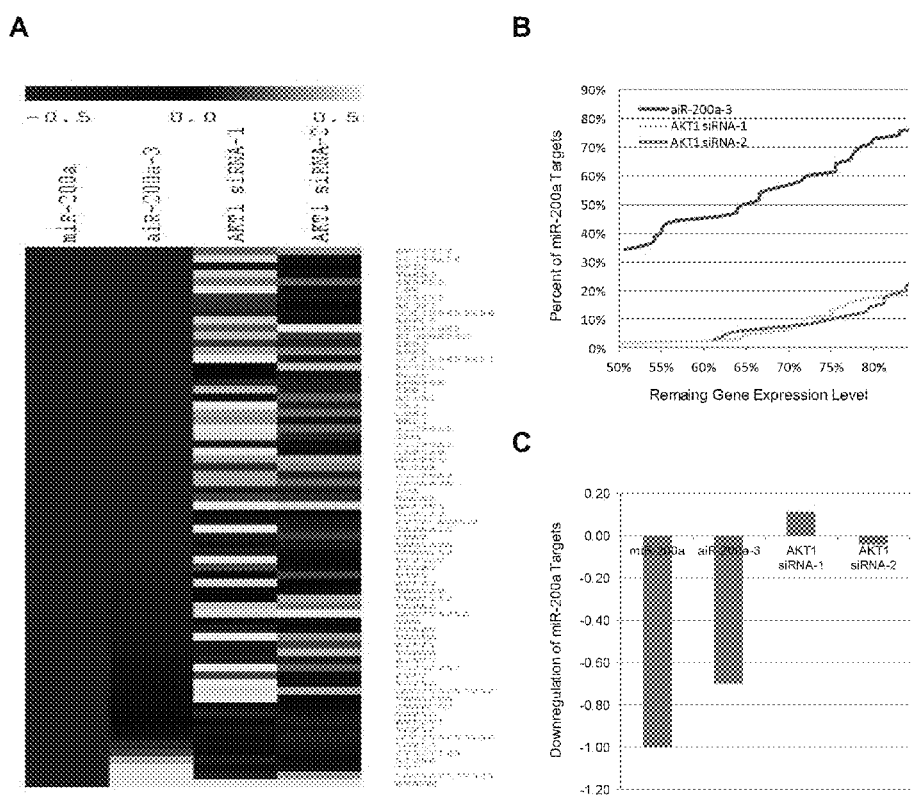
FIG. 4 depicts graphs showing global characterization of gene targets of aiRNA-200a with RNA-seq analysis. miR- 200a, aiR-200a-3 and two AKT1 siRNAs were individually transfected into HeLa cells and the global impact on the transcriptome was assessed with RNA-seq analysis. The sequencing data were normalized and log 2 transformed. Gene downregulation was determined by comparing to the negative control transfections. In this way, 70 gene targets of miR-200a (downregulated by at least 40%) were identified. (A) Expression profile of 70 genes targeted by miR-200a. The expression levels of these miR-200a targets were compared under various treatment conditions (i.e. overexpression of miR-200a, aiR-200a-3 or AKT1 siRNA) in order to identify gene targets shared by miR-200a and aiR-200a-3/siRNA. (B) Percentages of miR-200a targets that were also suppressed by aiR-200a-3 or AKT1 siRNA at various remaining expression levels. (C) Average level of suppression of miR-200a targets by miR-200a, aiR-200a-3 or AKT1 siRNAs.

Global gene target regulation by aiR-200a-3 was evaluated and compared to miR-200a and AKT1 siRNAs at the transcriptome level with RNA-seq analysis. With overexpression of miR-200a, 70 genes were downregulated by over 40%, including ZEB1 and ZEB2 that were also targeted by aiRNA-200a-3 as revealed by real-time RT-PCR (FIG. 4A). Among these 70 miR-200a targets, 62 were also downregulated by aiR-200a-3, including 31 targets downregulated by over 40% (FIG. 4B; listed in Table 1). In contrast, only a single miR-200a target (1.4% of total) was downregulated by over 40% by one of the two AKT1 siRNAs. Thus, most miR-200a targets were also targets of aiR-200a-3, but not AKT siRNAs. On average, these genes were suppressed to comparable levels, 50% and 38% by miR-200a and aiR-200a-3, respectively (FIG. 4C); in contrast, they were not suppressed by either of the two AKT1 siRNAs (108% and 97% of the negative control, respectively). In summary, both computational target prediction and RNA-seq validation data demonstrated the high similarity in global target regulation profiles by miR-200a and aiR-200a-3.

TABLE 1

Downregulation of 70 miR-200a targets as revealed by RNA-seq.

| Gene | miR-200a | aiR-200a-3 | AKT1 siRNA-1 | AKT1 siRNA-2 |
|---|---|---|---|---|
| ACOT7 | 40% | 34% | 75% | 77% |
| ACTA1 | 49% | 48% | 91% | 86% |
| ARPC5 | 41% | 37% | 76% | 80% |
| ATOH8 | 60% | 127% | 168% | 136% |
| C22orf23 | 59% | 110% | 159% | 130% |
| CBX1 | 49% | 48% | 92% | 87% |
| CDK6 | 49% | 49% | 93% | 88% |
| DCTN3 | 52% | 55% | 102% | 92% |
| DKK1 | 50% | 49% | 95% | 89% |
| DPY19L1 | 24% | 19% | 48% | 24% |
| DR1 | 52% | 61% | 107% | 94% |
| DTX3 | 55% | 75% | 125% | 106% |
| EVI5L | 58% | 90% | 136% | 121% |
| FAM158A | 54% | 68% | 116% | 104% |
| FAM220A | 59% | 93% | 140% | 123% |
| FAM35B | 48% | 43% | 87% | 85% |
| FAM72B | 55% | 76% | 126% | 107% |
| FLJ32255 | 57% | 89% | 136% | 116% |
| GEM | 50% | 53% | 97% | 90% |
| GNB1L | 59% | 95% | 142% | 124% |
| HINT3 | 57% | 88% | 135% | 116% |
| HMOX1 | 52% | 64% | 108% | 95% |
| HOXC13 | 53% | 65% | 110% | 98% |
| HS6ST2 | 39% | 34% | 72% | 75% |
| ITGB3 | 55% | 72% | 124% | 106% |
| KCTD20 | 47% | 42% | 87% | 84% |
| KIDINS220 | 43% | 40% | 79% | 81% |
| LBR | 34% | 32% | 71% | 73% |
| LOC100130331 | 60% | 158% | 180% | 146% |
| LOC100507032 | 58% | 92% | 138% | 121% |
| LOC100653106 | 40% | 35% | 75% | 79% |
| LOC100653136 | 59% | 103% | 155% | 126% |
| LOC100653311 | 45% | 41% | 87% | 84% |
| LOC729852 | 56% | 78% | 127% | 110% |
| LOXL3 | 59% | 106% | 157% | 127% |
| LRRC8B | 51% | 54% | 100% | 92% |
| MAP2K4 | 52% | 55% | 100% | 92% |
| MAP3K3 | 53% | 64% | 110% | 96% |
| NRP1 | 45% | 41% | 87% | 84% |
| NUP43 | 55% | 76% | 125% | 107% |
| PDGFA | 56% | 80% | 132% | 115% |
| PDHA1 | 55% | 77% | 127% | 109% |
| PDXP | 47% | 43% | 87% | 85% |
| PEX12 | 59% | 101% | 150% | 126% |
| PIF1 | 58% | 89% | 136% | 119% |
| PORCN | 56% | 83% | 134% | 116% |
| PPP3CC | 55% | 72% | 120% | 106% |
| PPT2 | 28% | 24% | 65% | 62% |
| PPT2-EGFL8 | 53% | 66% | 111% | 99% |
| RNF5P1 | 59% | 98% | 149% | 125% |
| SERPINE1 | 42% | 38% | 77% | 81% |
| SLC16A3 | 52% | 55% | 106% | 92% |
| SLC30A1 | 51% | 54% | 97% | 91% |
| SLC35D1 | 50% | 51% | 95% | 89% |
| SLC39A10 | 28% | 23% | 64% | 61% |
| SMARCD3 | 59% | 93% | 141% | 124% |
| SNRPB2 | 32% | 31% | 71% | 68% |
| SRM | 56% | 78% | 130% | 111% |
| TMEM158 | 54% | 70% | 117% | 106% |
| TRMT112 | 55% | 77% | 127% | 108% |
| TSPAN12 | 53% | 67% | 112% | 101% |
| TST | 60% | 145% | 170% | 144% |
| TUBB8 | 56% | 80% | 131% | 114% |
| UBASH3B | 52% | 57% | 106% | 94% |
| UPRT | 54% | 67% | 112% | 102% |
| WHAMM | 60% | 198% | 195% | 160% |
| WIPI1 | 56% | 83% | 133% | 115% |
| YWHAG | 31% | 30% | 69% | 63% |
| ZEB1 | 49% | 47% | 91% | 85% |
| ZEB2 | 44% | 40% | 85% | 82% |

Gene downregulation was determined by referencing to the average readings of the negative control samples.

Example 5

Multi-Functional Suppression of Cancer Cells by aiR-200a

Figure 5:
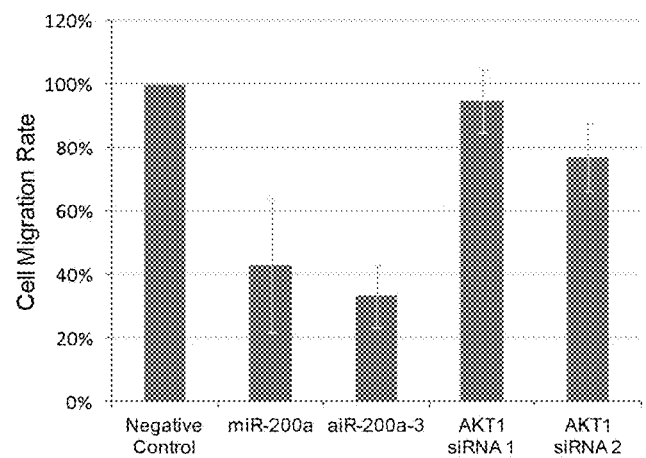
FIG. 5 depicts graphs showing functional characterization of aiR-200a for suppression of both the motility and proliferation of cancer cells. miR-200a, aiR-200a-3 or two AKT1 siRNAs were individually transfected into HeLa cells and changes in cell motility or proliferation were determined by comparing to the negative control transfections. (A) Transwell migration assays to assess changes in cell motility. (B) MTS assays to assess changes in cell proliferation.
Figure 5:
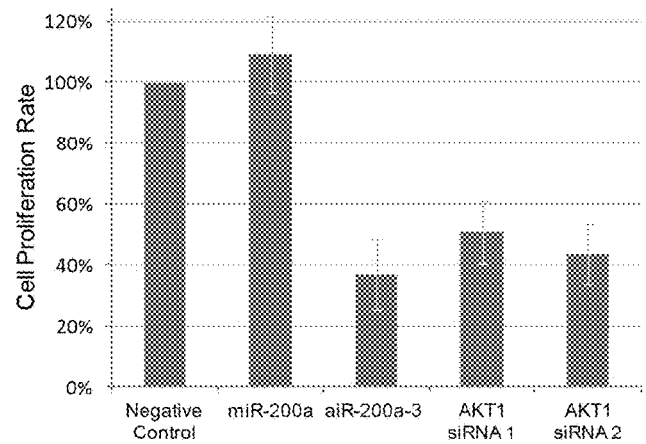

By targeting multiple genes involved in EMT regulation (including ZEB1 and ZEB2), miR-200a can suppress the motility of cancer cells. Similarly, by mimicking miR-200a and targeting similar sets of genes, aiR-200a was also expected to be a suppressor for cell motility. This hypothesis was tested experimentally with transwell cell migration assays. aiR-200a-3 was overexpressed in HeLa cells and the impact on cell motility was compared to miR-200a, AKT1 siRNAs and negative controls. As shown in FIG. 5A, both aiR-200a-3 and miR-200a, but not AKT1 siRNAs, were able to significantly suppress cell migration by about 60%. Thus, by mimicking miR-200a, aiR-200a-3 inherited the function from miR-200a for suppression of cancer cell motility.

Figure 3:
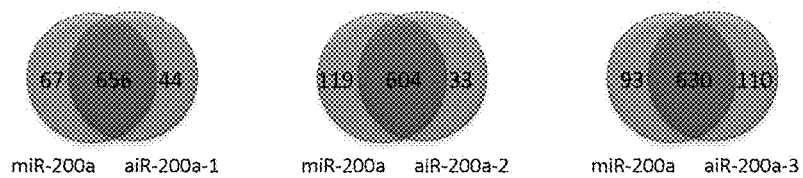
FIG. 3 depicts sequences, graphs and a immunoblot showing the design and validation of aiRNA-200a. (A) Sequences of three aiR-200a RNAs. These aiRNAs were designed to share the same seed sequence with miR-200a, as well as have high sequence homology to three distinct AKT1 siRNAs, respectively. The seed regions are underlined. Bases that are different from the corresponding siRNAs are highlighted in red. miR-200a (SEQ ID NO:1—UAACACUGUCUGGUAACGAUGU); aiR-200a-1 (SEQ ID NO:6—UAACACUGCCCUACGUGAAUC); aiR-200a-2 (SEQ ID NO:7—UAACACUGUUAAACCUUGCUC); aiR-200a-3 (SEQ ID NO:8—UAACACUGCUCCUCUGUCCCA) (B) Comparison of predicted gene targets by miR-200a and aiR-200a. MirTarget2 was employed for the prediction of genes targeted by miR-200a and three aiR-200a RNAs, respectively. Each aiR-200a RNA was compared to miR-200a for predicted target overlap. (C) Real-time PCR to validate predicted target suppression by miR-200a and aiR-200a. mRNA expression of three genes was assessed, including AKT1 and two previously validated targets of miR-200a, ZEB1 and ZEB2. miR-200a, three aiR-200a RNAs and two AKT1 siRNAs were individually transfected into HeLa cells and target gene expression was determined by comparing to the negative control transfections. (D) Western blotting to evaluate suppression of AKT1 protein expression by miR-200a, aiR-200a RNAs or AKT1 siRNAs in HeLa cells.
Figure 3:
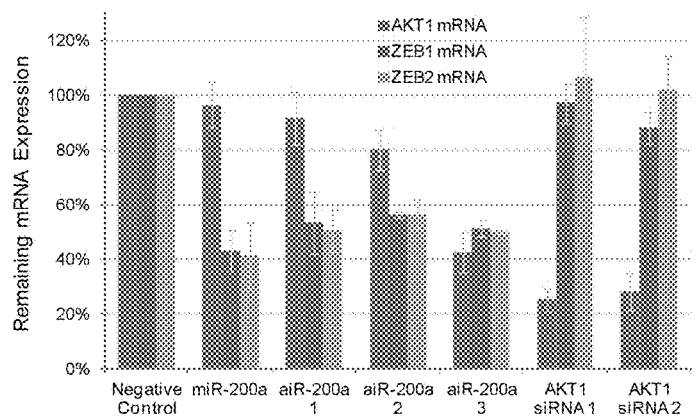
Figure 3:
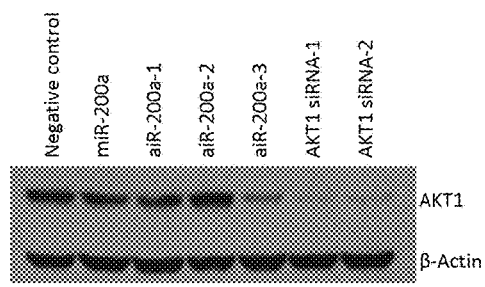

A newly gained function of aiR-200a-3 by in silico design was the ability to suppress cancer cell proliferation through targeting AKT1. To test this additional function, MTS cell proliferation assays were performed to evaluate the anti-proliferation potential of aiR-200a-3, which was capable of suppressing AKT1 expression (FIG. 3). Similar to AKT1 siRNAs, overexpression of aiR-200a-3 led to a significant reduction of cell proliferation rate by about 60% (FIG. 5B). In contrast, overexpression of miR-200a had no impact on cell proliferation. Thus, aiR-200a-3 was able to simultaneously suppress both cancer cell migration and proliferation, whereas miR-200a and AKT1 siRNA were only able to suppress either cell migration or proliferation, but not both.

Example 6

Expression of aiR-200a-3

For aiR-200a-3, we have also designed hairpin shRNAs to stably express the aiRNA using a lentiviral delivery system (pLKO.1, http://www.addgene.org/8453/). The hairpin designs are presented in FIG. 8, with the aiR-200a-3 sequence highlighted in red. In brief, the DNA oligos were ordered from Sigma-Aldrich, annealed and then ligated into the pLKO.1 expression vector. Lentiviral particles were packaged in 293T cells. The virus-containing cell culture supernatant was collected and used to infect other mammalian cell lines. Infected cells were selected by puromycin for shRNA expression. In contrast to transient transfection using synthetic aiRNA, the shRNA expression system allows long-term stable expression of aiRNA in the cells. We have also tested the functions of these aiR-200a-expressing shRNAs with migration and proliferation assays (described in Example 5). Similar to synthetic aiR-200a-3, long-term expression of aiR-200a shRNAs led to reduced rates of cancer cell proliferation and migration.

Example 7

Additional Design of Multi-Functional aiRNAs by Mimicking Both miR-9 and TP53 siRNA We further tested the hypothesis that the principles used for aiR-200a design can be generalized for the design of other aiRNA species by mimicking other miRNAs and siRNAs. To this end, aiR-9 aiRNAs mimicking both miR-9 and TP53 siRNAs were designed. miR-9 is capable of promoting cancer cell motility as shown in previous studies (Ma et al. 2010; Wang et al. 2011), and TP53 is a well-characterized tumor suppressor that promotes cancer cell death under chemotherapy. Thus, by mimicking both miR-9 and TP53 siRNA, aiR-9 was expected to resemble a "hyper-functional oncogene" by promoting cancer cell motility and also avoiding cell death under chemotherapy. Although not practically useful as far as cancer cell killing is concerned, successful design of aiR-9 nevertheless would show that the general principles of aiRNA design can be broadly applied to flexibly engineer new small RNAs targeting different combinations of cellular functions.

Figure 6:
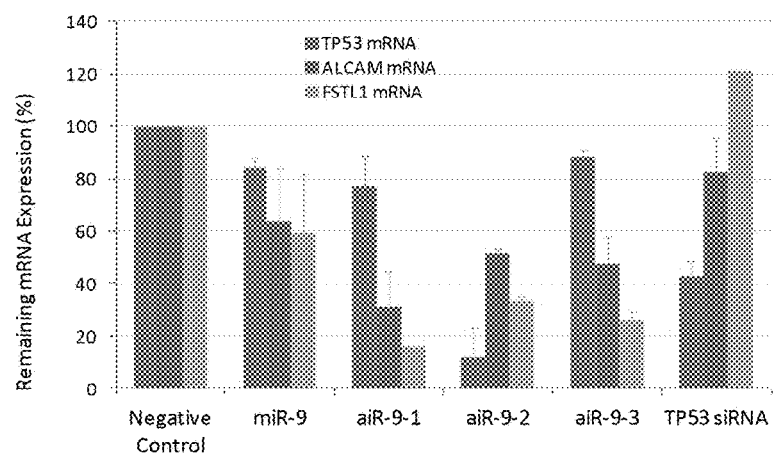
FIG. 6 depicts sequences and a graph showing design and validation of aiRNA-9. (A) Sequences of three aiR-9 RNAs. These aiRNAs were designed to share the same seed sequence with miR-9, as well as have high sequence homology to three distinct TP53 siRNAs, respectively. The seed regions are underlined. Bases that are different from the corresponding siRNAs are highlighted in red. miR-9 (SEQ ID NO:9—UCUUUGGUUAUCUAGCUGUAUGA); aiR-9-1 (SEQ ID NO:10—UCUUUGGUUAGUACGGUGAAG); aiR-9-2 (SEQ ID NO:11—UCUUUGGUUGGGGAGAGGAGC); aiR-9-3 (SEQ ID NO:12—UCUUUGGUCCCAGCUACUCCG) (B) Real-time PCR to validate predicted target suppression by aiR-9. mRNA expression of three genes was assessed, including TP53 and two previously validated targets of miR-9, ALCAM and FSTL1. miR-9, three aiR-9 RNAs and TP53 siRNA were individually transfected into HeLa cells and target gene expression was determined by comparing to the negative control transfections.

As the first step of aiR-9 design, the siOligo algorithm was used to select potent siRNAs targeting TP53 (Wang et al. 2009), as similarly described in detail for the design of aiR-200a. Then, candidate aiR-9 sequences were designed by replacing the seed region of the siRNA sequences with miR-9 seed. In this way, three aiR-9 RNAs were designed, with 1-2 mismatches in the seed region to the corresponding TP53 siRNAs (FIG. 6A).

Figure 7:
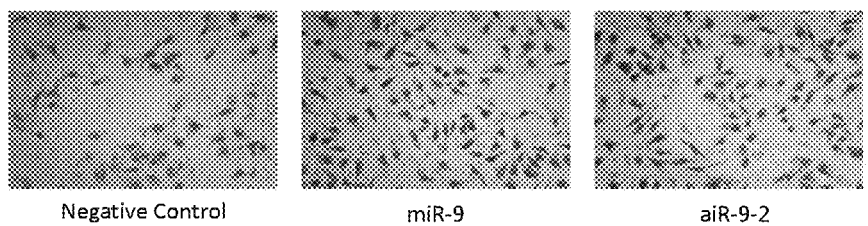
FIG. 7 depicts images and graphs showing functional characterization of aiR-9 on cell motility and cell death. (A) Impact of aiR-9 on cell motility. miR-9, aiR-9-2 and negative control RNA were individually transfected into HeLa cells and changes in cell motility was determined by transwell migration assay. miR-9 and aiR-9-2 overexpression led to increased cell mobility to 144% and 157% on average, respectively as compared to the control. One representative microscope image from each assay is presented here. (B) Impact of aiR-9 on cell death. TP53 deficiency renders HCT116 cells resistance to cisplatin-induced cell death. HCT116 cells and HCT116 p53$^{-/-}$ cells were treated with cisplatin (50 µM) and cell death was determined as sub-G1 population by flow cytometry analysis after DNA PI staining. Furthermore, HCT116 cells were transfected with negative control RNA, aiR-9-2 or miR-9 individually followed by cisplatin treatment, and then analyzed by flow cytometry for cell death with PI staining.
Figure 7:
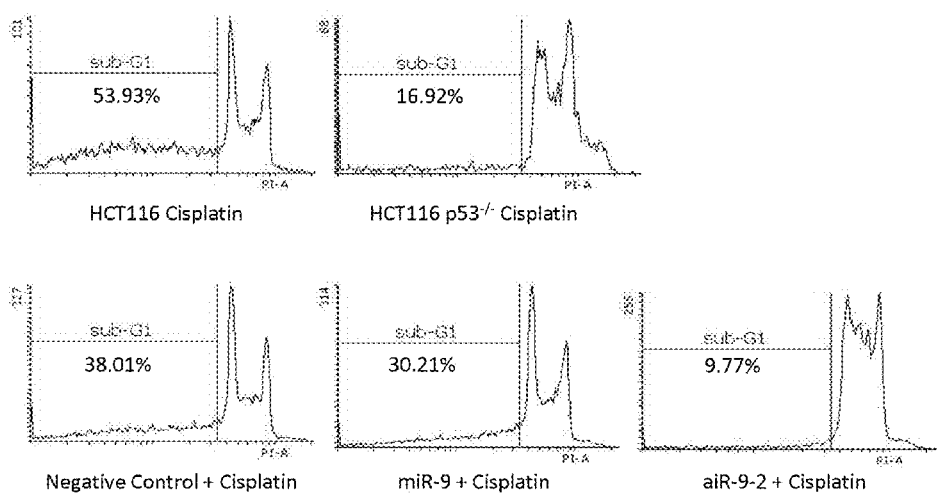

We evaluated the impact of aiR-9 on regulating the expression of TP53, as well as two previously validated miR-9 targets, ALCAM 9 (Wang et al. 2011) and FSTL1 (both are involved in regulating cell motility, manuscript in preparation) by real-time RT-PCR. As shown in FIG. 6B, all three aiR-9 RNAs, but not TP53 siRNA, were able to significantly suppress the expression of both targets of miR-9. However, only one aiR-9, aiR-9-2 was also able to effectively suppress the expression of TP53. Thus, aiR-9-2 was selected for further functional validation as it met our design goal of suppressing both TP53 and selected miR-9 targets. The impact of aiR-9 on cell motility was evaluated in HeLa cells, in which TP53 functions were abrogated by HPV-induced protein degradation (Scheffner et al. 1990). As shown in FIG. 7A, both miR-9 and aiR-9-2 were able to significantly promote cell motility by 44% and 57%, respectively, as compared to the negative control. Thus, as expected by design, aiR-9-2 inherited the ability from miR-9 for promoting cell mobility. On the other hand, aiR-9 was also able to resemble the phenotype of TP53 knockout (TP53$^{-/-}$) in HCT116 cells, as both aiR-9 overexpression and TP53 knockout led to drastic suppression of cisplatin-induced cell death as evaluated by flow cytometry analysis of sub-G1 cell population (FIG. 7B).

Discussion for the Examples

As a single miRNA can regulate a large number of gene targets, miRNAs can potentially function as master switches to regulate a large portion of gene regulatory networks. The ability of multi-targeting by miRNAs is important to simultaneously regulate multiple potentially redundant biological pathways, leading to observable cellular phenotypes. Thus, miRNAs have been intensely studied as potential therapeutic agents to treat a variety of human diseases. Based on the clinical importance of miRNAs, we further proposed to design aiRNAs as an improved strategy for disease treatment. Our approach may potentially alleviate the dependency on a limited number of natural miRNAs by rationally designing and testing a large number of aiRNAs for improved therapeutic efficacy. In our study, we have shown that an aiRNA mimicking miR-200a not only inherited the anti-metastatic capacity of miR-200a, but also gained the new function of anti-proliferation by mimicking an AKT1 siRNA. Thus, the aiRNA is considered to function equivalently to a combination of miR-200a and AKT1 siRNA. The general design principles were further validated by testing aiRNAs that mimic both miR-9 and TP53 siRNA.

A major advantage of a single multi-functional aiRNA compared with multiple miRNAs or siRNAs is that there are fewer small RNA molecules that compete for entering the RNAi machinery, thereby minimizing potential toxicity effects (Grimm et al. 2006; Jackson and Linsley 2010). In addition, distinct sequences from multiple combined miR-NAs/siRNAs will significantly boost undesired sequence-specific off-target effects. Furthermore, the inclusion of a single aiRNA (in contrast to multiple miRNAs/siRNAs) will greatly simplify the therapeutic delivery process, as the pharmacokinetics and pharmacodynamics of every miRNA or siRNA included in delivery has to be closely monitored. In summary, a single multi-functional aiRNA is likely to be a more effective approach involving fewer potential side effects.

Relevant to our work, recent studies have proposed alternative designs of multi-target small RNAs to suppress a pair of distinct gene targets by utilizing two active strands in an siRNA duplex, or suppress several functionally redundant genes from the same family by targeting homologous binding sites in the transcripts (De Guire et al. 2010; Tiemann et al. 2010; Saetrom 2013). For these design strategies, the number of intended targets is limited. In contrast, we propose to employ the seed sequence of natural miRNAs for aiRNA design, thus inheriting the functions of miRNAs by suppressing many intended miRNA targets. As shown by both bioinformatics and RNA-seq analyses, the target profiles of seed-sharing aiRNA and miRNA are highly similar. Therefore, undesired off-target effects from aiRNAs will be greatly reduced. Our aiRNA design strategy is expected to be useful for the development of new RNAi therapeutics, in which multiple genes need to be targeted simultaneously. This represents a potentially potent strategy for more effective disease control such as triggering synthetic lethality in cancer treatment. Our aiRNA design principle can be generalized to broadly target other human diseases in addition to cancer.

Previous studies indicate that an siRNA with a few mismatched bases to the target binding site may still potentially suppress the expression of its intended gene target. However, no well-defined rules have been established to correlate siRNA knockdown efficiency to the composition of mismatches in the seed region. In our limited analysis of three aiRNAs designed to target AKT1, one inherited the knockdown capacity from the corresponding siRNA, despite the presence of two contiguous mismatched bases. In contrast, the other aiRNAs were unable to knockdown AKT1, due to either three contiguous mismatches or two interspersed mismatches. Thus, it seems that both the number and positions of the mismatches in the seed region can impact aiRNA knockdown efficiency in an siRNA-like fashion. A similar design success rate was also observed when designing aiRNAs to target TP53. To further improve design success rate, a large number of aiRNAs with various mismatch compositions would need to be analyzed experimentally in the future to elucidate the rules of mismatch tolerance, which would eventually lead to significant algorithmic improvement.

In our study, siRNAs are considered as a special form of aiRNA, and they share similar characteristics with miRNAs and other types of aiRNA for multi-targeting, which is commonly known as siRNA off-target effects. Off-targeting is an intrinsic property of siRNAs and thus its impact should be thoroughly considered in RNAi therapeutics. Our work indicated that, by modifying the seed region of an siRNA, we were able to convert unintended off-target effects into intended miRNA-like "on-target" suppression. This provides new insights into the design of potent siRNA-based therapeutics by utilizing the multi-target nature of siRNAs. Although miRNAs and siRNAs are still two distinct therapeutic strategies at present, we envision that the boundary defining the two would be blurred in future, as it is possible to design aiRNAs that combine the advantages of both miRNAs and siRNAs for RNAi-based therapeutics.

Materials and Methods for the Examples

Cell Transfection.

HeLa cells or HCT116 cells were transfected with synthetic miRNAs or siRNAs (Sigma-Aldrich) and Lipofectamine 2000 (Life Technologies). Negative controls included both transfection with a negative control small RNA (with a random sequence) and transfection with no RNA added, and the average readings from both control transfections were used as the baseline reference for evaluating the impact of miRNA or siRNA overexpression. GAPDH siRNA was used as a positive control to monitor the transfection efficiency by real-time RT-PCR. Total RNA was extracted 24 h post transfection using the mirVana RNA Isolation Kit (Life Technologies).

Real-Time RT-PCR.

Reverse transcription was performed with the High Capacity RT kit (Life Technologies). All PCR primers were designed in our previous study and the sequences were retrieved from PrimerBank (Wang et al. 2012). Real-time PCR was performed to determine the relative expression levels of the transcripts. The PCR running protocol was the same as previously described (Wang and Seed 2003). Both GAPDH and β-actin were used as internal controls for gene expression normalization.

Western Blot.

Cells were harvested and lysed in RIPA buffer (Thermo Scientific) and protease inhibitor mixture tablet (Roche Applied Science). The lysate was then centrifuged, and protein supernatant was applied to SDS-PAGE. Separated protein bands on the gel were transferred to Immun-Blot PVDF membrane (Bio-Rad). The membrane was first blocked with 5% non-fat milk in Tris-buffered saline (TBS, pH 7.4) and then incubated with primary anti-AKT1 mAb (Cell Signaling) or anti-β-Actin mAb (Sigma-Aldrich). After washing with TBS, the blots were incubated with secondary anti-mouse IgG mAb conjugated with horseradish peroxidase (Thermo Scientific). Bound antibodies were visualized by HRP substrate (Millipore) and chemiluminescent signal was detected on X-ray films.

Transwell Migration Assay.

Cultured cells were resuspended and washed with PBS buffer. Fifty thousand cells in 100 μL serum-free medium were added to the upper chamber of each Transwell (24-well insert with 8 um pore size from Costar). The lower chamber was filled with 600 μL medium containing 10% bovine serum. Cells were incubated for 6 h and cells on top of the membrane were removed with a cotton-tipped swab. Cells that had migrated through the membrane were fixed and stained with Hema-3 (Fisher Scientific) for counting.

Cell Proliferation Assay.

Three days after transfection, cell proliferation rate was determined with the MTS kit (Promega). In brief, 10 μL of MTS substrate was added into each well containing 100 μL of 10% FBS medium in a 96-well plate. The plate was then incubated for 3 h and the signal was measured using a BioTek ELx800 microplate reader.

Microarray.

Microarrays were performed at the Washington University Genome Center using the Illumina BeadChip platform. The RNA quality was assessed by Agilent 2100 Bioanalyzer (Agilent Technologies). The RNA was first amplified with the MessageAmp Total Prep kit (Life Technologies). Amplified RNA samples were then applied to BeadChip arrays according to the manufacture's protocols for hybridization and washing. Arrays were scanned with Illumina BeadArray Reader, and images were analyzed by Illumina Beadscan and Beadstudio software. On-slide spot replicates were averaged and reported. Raw array data were normalized using the quantile normalization method. The microarray data were deposited in the NCBI GEO database.

RNA-Seq.

Total RNA was used to construct cDNA libraries for high-throughput RNA sequencing. First, ribosomal RNA (rRNA) was removed using the RiboMinus kit (Life Technologies) and custom designed rRNA oligonucleotide probes, following the manufacture's protocol. rRNA-depleted total RNA was then used as template to construct RNA-seq libraries with the NEBNext mRNA Library Prep kit (New England BioLabs). In brief, double-stranded cDNA was synthesized from rRNA-depleted total RNA, end repaired, dA tailed, and then ligated to standard Illumina adaptor oligos. Adaptor-ligated cDNA libraries were amplified using Phusion PCR master mix. Amplified cDNA libraries were loaded into HiSeq 2000 (Illumina) for sequencing at the Washington University Genome Center. The resulting raw sequence reads were preprocessed with a custom bioinformatics pipeline to remove low-quality reads and clustered before mapping to the human transcriptome and genome (version 19) with Bowtie (Langmead et al. 2009). In this way, about 90% of all sequence reads were mapped to human sequences. Sequence reads mapped to the same transcript were combined and then normalized by the length of the transcript as well as the number of total reads from each sample (reads per kb per million, RPKM). Normalized read counts were compared across samples to assess changes in transcript abundance, and listed in Supplementary Table 2. Transcripts from the same gene locus were combined for evaluation of expression changes at the gene level.

Flow Cytometry.

HCT116 and HCT116 $p53^{-/-}$ cells were cultured in DMEM with 10% FBS. Cisplatin, DNase-free RNase and Propidium Iodide (PI) were purchased from Sigma. After treatment with cisplatin (50 µM), all cells (both floating and attached) were collected, washed once with DPBS, and then fixed with 70% ethanol on ice for at least 30 minutes. Fixed cells were washed twice with DPBS and then stained with PI solution [PI (25 µg/ml) and DNase-free RNase (100 µg/ml) diluted in PBS] at room temperature for 1 hour avoiding light exposure. Data were acquired by BD Aris FACS and analyzed using Flowing Software 2 version 2.5.0 (Finland).

REFERENCES FOR THE EXAMPLES

1. Ambros, V. 2004. The functions of animal microRNAs. *Nature* 431: 350-355.
2. Anderson, E. M., Birmingham, A., Baskerville, S., Reynolds, A., Maksimova, E., Leake, D., Fedorov, Y., Karpilow, J., and Khvorova, A. 2008. Experimental validation of the importance of seed complement frequency to siRNA specificity. *RNA* 14: 853-861.
3. Bellacosa, A., Kumar, C. C., Di Cristofano, A., and Testa, J. R. 2005. Activation of AKT kinases in cancer: implications for therapeutic targeting. *Adv Cancer Res* 94: 29-86.
4. Birmingham, A., Anderson, E. M., Reynolds, A., Ilsley-Tyree, D., Leake, D., Fedorov, Y., Baskerville, S., Maksimova, E., Robinson, K., Karpilow, J. et al. 2006. 3' UTR seed matches, but not overall identity, are associated with RNAi off-targets. *Nat Methods* 3: 199-204.
5. Calin, G. A., and Croce, C. M. 2006. MicroRNA signatures in human cancers. *Nat Rev Cancer* 6: 857-866.
6. Croce, C. M. 2009. Causes and consequences of microRNA dysregulation in cancer. *Nat Rev Genet* 10: 704-714.
7. De Guire, V., Caron, M., Scott, N., Menard, C., Gaumont-Leclerc, M. F., Chartrand, P., Major, F., and Ferbeyre, G. 2010. Designing small multiple-target artificial RNAs. *Nucleic Acids Res* 38: e140.
8. Denli, A. M., and Hannon, G. J. 2003. RNAi: an ever-growing puzzle. *Trends Biochem Sci* 28: 196-201.
9. Gregory, P. A., Bert, A. G., Paterson, E. L., Barry, S. C., Tsykin, A., Farshid, G., Vadas, M. A., Khew-Goodall, Y., and Goodall, G. J. 2008. The miR-200 family and miR-205 regulate epithelial to mesenchymal transition by targeting ZEB1 and SIP1. *Nat Cell Biol* 10: 593-601.
10. Grimm, D., Streetz, K. L., Jopling, C. L., Storm, T. A., Pandey, K., Davis, C. R., Marion, P., Salazar, F., and Kay, M. A. 2006. Fatality in mice due to oversaturation of cellular microRNA/short hairpin RNA pathways. *Nature* 441: 537-541.
11. Hannon, G. J. 2002. RNA interference. *Nature* 418: 244-251.
12. Jackson, A. L., Bartz, S. R., Schelter, J., Kobayashi, S. V., Burchard, J., Mao, M., Li, B., Cavet, G., and Linsley, P. S. 2003. Expression profiling reveals off-target gene regulation by RNAi. *Nat Biotechnol* 21: 635-637.
13. Jackson, A. L., Burchard, J., Leake, D., Reynolds, A., Schelter, J., Guo, J., Johnson, J. M., Lim, L., Karpilow, J., Nichols, K. et al. 2006. Position-specific chemical modification of siRNAs reduces "off-target" transcript silencing. *RNA* 12: 1197-1205.
14. Jackson, A. L., and Linsley, P. S. 2010. Recognizing and avoiding siRNA off-target effects for target identification and therapeutic application. *Nat Rev Drug Discov* 9: 57-67.
15. Johnson, C. D., Esquela-Kerscher, A., Stefani, G., Byrom, M., Kelnar, K., Ovcharenko, D., Wilson, M., Wang, X., Shelton, J., Shingara, J. et al. 2007. The let-7 microRNA represses cell proliferation pathways in human cells. *Cancer Res* 67: 7713-7722.
16. Kent, O. A., and Mendell, J. T. 2006. A small piece in the cancer puzzle: microRNAs as tumor suppressors and oncogenes. *Oncogene* 25: 6188-6196.
17. Kota, J., Chivukula, R. R., O'Donnell, K. A., Wentzel, E. A., Montgomery, C. L., Hwang, H. W., Chang, T. C., Vivekanandan, P., Torbenson, M., Clark, K. R. et al. 2009. Therapeutic microRNA delivery suppresses tumorigenesis in a murine liver cancer model. *Cell* 137: 1005-1017.
18. Kozomara, A., and Griffiths-Jones, S. 2011. miRBase: integrating microRNA annotation and deep-sequencing data. *Nucleic Acids Res* 39: D152-157.
19. Langmead, B., Trapnell, C., Pop, M., and Salzberg, S. L. 2009. Ultrafast and memory-efficient alignment of short DNA sequences to the human genome. *Genome Biol* 10: R25.
20. Lewis, B. P., Burge, C. B., and Bartel, D. P. 2005. Conserved seed pairing, often flanked by adenosines, indicates that thousands of human genes are microRNA targets. *Cell* 120: 15-20.
21. Lim, L. P., Lau, N. C., Garrett-Engele, P., Crimson, A., Schelter, J. M., Castle, J., Bartel, D. P., Linsley, P. S., and Johnson, J. M. 2005. Microarray analysis shows that some microRNAs downregulate large numbers of target mRNAs. *Nature* 433: 769-773.
22. Ma, L., Young, J., Prabhala, H., Pan, E., Mestdagh, P., Muth, D., Teruya-Feldstein, J., Reinhardt, F., Onder, T. T., Valastyan, S. et al. 2010. miR-9, a MYC/MYCN-activated microRNA, regulates E-cadherin and cancer metastasis. *Nat Cell Biol* 12: 247-256.

23. Mestdagh, P., Lefever, S., Pattyn, F., Ridzon, D., Fredlund, E., Fieuw, A., Ongenaert, M., Vermeulen, J., De Paepe, A., Wong, L. et al. 2011. The microRNA body map: dissecting microRNA function through integrative genomics. *Nucleic Acids Res* 39: e136.
24. Miranda, K. C., Huynh, T., Tay, Y., Ang, Y. S., Tam, W. L., Thomson, A. M., Lim, B., and Rigoutsos, I. 2006. A pattern-based method for the identification of MicroRNA binding sites and their corresponding heteroduplexes. *Cell* 126: 1203-1217.
25. Miska, E. A. 2005. How microRNAs control cell division, differentiation and death. *Curr Opin Genet Dev* 15: 563-568.
26. Nielsen, C. B., Shomron, N., Sandberg, R., Hornstein, E., Kitzman, J., and Burge, C. B. 2007. Determinants of targeting by endogenous and exogenous microRNAs and siRNAs. *RNA* 13: 1894-1910.
27. Park, S. M., Gaur, A. B., Lengyel, E., and Peter, M. E. 2008. The miR-200 family determines the epithelial phenotype of cancer cells by targeting the E-cadherin repressors ZEB1 and ZEB2. *Genes Dev* 22: 894-907.
28. Rossi, J. J. 2009. New hope for a microRNA therapy for liver cancer. *Cell* 137: 990-992.
29. Saetrom, P. 2013. Designing dual-targeting sRNA duplexes having two active strands that combine sRNA and microRNA-like targeting. *Methods Mol Biol* 942: 169-177.
30. Scheffner, M., Werness, B. A., Huibregtse, J. M., Levine, A. J., and Howley, P. M. 1990. The E6 oncoprotein encoded by human papillomavirus types 16 and 18 promotes the degradation of p53. *Cell* 63: 1129-1136.
31. Sontheimer, E. J. 2005. Assembly and function of RNA silencing complexes. *Nat Rev Mol Cell Biol* 6: 127-138.
32. Tiemann, K., Hohn, B., Ehsani, A., Forman, S. J., Rossi, J. J., and Saetrom, P. 2010. Dual-targeting siRNAs. *RNA* 16: 1275-1284.
33. Tong, A. W., and Nemunaitis, J. 2008. Modulation of miRNA activity in human cancer: a new paradigm for cancer gene therapy? *Cancer Gene Ther* 15: 341-355.
34. Valastyan, S., Reinhardt, F., Benaich, N., Calogrias, D., Szasz, A. M., Wang, Z. C., Brock, J. E., Richardson, A. L., and Weinberg, R. A. 2009. A pleiotropically acting microRNA, miR-31, inhibits breast cancer metastasis. *Cell* 137: 1032-1046.
35. Wang, J., Gu, Z., Ni, P., Qiao, Y., Chen, C., Liu, X., Lin, J., Chen, N., and Fan, Q. 2011. NF-kappaB P50/P65 hetero-dimer mediates differential regulation of CD166/ALCAM expression via interaction with micoRNA-9 after serum deprivation, providing evidence for a novel negative auto-regulatory loop. *Nucleic Acids Res* 39: 6440-6455.
36. Wang, X. 2008. miRDB: a microRNA target prediction and functional annotation database with a wiki interface. *RNA* 14: 1012-1017.
37. Wang, X., and El Naqa, I. M. 2008. Prediction of both conserved and nonconserved microRNA targets in animals. *Bioinformatics* 24: 325-332.
38. Wang, X., and Seed, B. 2003. A PCR primer bank for quantitative gene expression analysis. *Nucleic Acids Res* 31: e154.
39. Wang, X., Spandidos, A., Wang, H., and Seed, B. 2012. PrimerBank: a PCR primer database for quantitative gene expression analysis, 2012 update. *Nucleic Acids Res* 40: D1144-1149.
40. Wang, X., Wang, X., Varma, R. K., Beauchamp, L., Magdaleno, S., and Sendera, T. J. 2009. Selection of hyperfunctional siRNAs with improved potency and specificity. *Nucleic Acids Res* 37: e152.
41. Wurdinger, T., and Costa, F. F. 2007. Molecular therapy in the microRNA era. *Pharmacogenomics J* 7: 297-304.

What is claimed is:

1. A composition, the composition comprising a nucleic acid construct comprising a nucleotide sequence of about 19 to about 25 nucleotides in which nucleotides 2 through 8 are identical to nucleotides 2 through 8 of an miRNA and the rest of the nucleotides are identical to those of a siRNA that specifically hybridizes to a target nucleic acid, wherein nucleotides 2 through 8 are capable of specifically hybridizing to nucleic acids that are naturally regulated by the miRNA and the entire nucleic acid construct is capable of specifically hybridizing to the target nucleic acid targeted by the siRNA.

2. The composition of claim 1, wherein the siRNA targets AKT1 and the miRNA is miR-200a.

3. The composition of claim 1, wherein nucleotides 2 through 8 of the siRNA sequence have 1, 2, or 3 mismatches relative to nucleotides 2 through 8 of the construct.

4. The composition of claim 3, wherein the mismatches are either interspersed or contiguous.

5. The composition of claim 3, wherein the mismatches are located within nucleotides 5 through 8.

6. The composition of claim 1, wherein the nucleotide sequence comprises a sequence selected from the group consisting of SEQ ID NO:6, SEQ ID NO:7, SEQ ID NO:8, nucleotides 37-57 of SEQ ID NO:13, and nucleotides 36-56 of SEQ ID NO:15.

7. The composition of claim 1, wherein the construct is a DNA that codes for the RNA.

* * * * *

UNITED STATES PATENT AND TRADEMARK OFFICE
CERTIFICATE OF CORRECTION

PATENT NO. : 9,550,989 B2
APPLICATION NO. : 14/506131
DATED : January 24, 2017
INVENTOR(S) : Xiaowei Wang It is certified that error appears in the above-identified patent and that said Letters Patent is hereby corrected as shown below:

In the Specification

Corrected Government Support Paragraph at Column 1, Lines 14-16 should read:

This invention was made with government support under Grant GM089784 awarded by the National Institutes of Health. The government has certain rights in the invention.

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*